United States Patent
Takahashi et al.

(10) Patent No.: US 9,394,514 B2
(45) Date of Patent: Jul. 19, 2016

(54) CULTURE SUBSTRATE, CULTURE SHEET, AND CELL CULTURE METHOD

(75) Inventors: Ryosuke Takahashi, Kawagoe (JP); Akiko Hisada, Kawagoe (JP); Hiroshi Sonoda, Tsurugashima (JP); Taku Saito, Tokyo (JP)

(73) Assignee: Hitachi, Ltd., Tokyo (JP)

(*) Notice: Subject to any disclaimer, the term of this patent is extended or adjusted under 35 U.S.C. 154(b) by 94 days.

(21) Appl. No.: 13/379,416

(22) PCT Filed: Jun. 22, 2010

(86) PCT No.: PCT/JP2010/004145
§ 371 (c)(1),
(2), (4) Date: Dec. 20, 2011

(87) PCT Pub. No.: WO2010/150521
PCT Pub. Date: Dec. 29, 2010

(65) Prior Publication Data
US 2012/0100612 A1    Apr. 26, 2012

(30) Foreign Application Priority Data

Jun. 23, 2009  (JP) ................................ 2009-148680
May 7, 2010   (JP) ................................ 2010-107331

(51) Int. Cl.
*C12M 3/00*    (2006.01)
*C12N 5/00*    (2006.01)
(Continued)

(52) U.S. Cl.
CPC .............. *C12N 5/0062* (2013.01); *C12M 21/08* (2013.01); *C12M 23/12* (2013.01); *C12M 25/06* (2013.01); *C12N 2535/10* (2013.01)

(58) Field of Classification Search
CPC ...... C12M 21/08; C12M 23/10; C12M 23/12; C12M 25/06

USPC ........... 435/287.2, 299.2, 297.5, 305.2, 288.4
See application file for complete search history.

(56) References Cited

U.S. PATENT DOCUMENTS

2003/0104494 A1*  6/2003  Ravkin et al. .................. 435/7.9
2005/0101010 A1   5/2005  Li
(Continued)

FOREIGN PATENT DOCUMENTS

JP    2005-312343 A   11/2005
JP    2006-121991 A   5/2006
(Continued)

OTHER PUBLICATIONS

Nomura et al. "Nanopillar sheets as a new type of cell culture dish: detailed study of HeLa cells cultured on nanopillar sheets". J. Artif. Organs (2006) vol. 9, pp. 90-96.*
(Continued)

*Primary Examiner* — William H Beisner
(74) *Attorney, Agent, or Firm* — Mattingly & Malur, PC

(57) ABSTRACT

Disclosed is a culture sheet which enables technology in which three-dimensional tissues with uniform diameter are formed without applying chemicals to the surface of a culture substrate. A plurality of holes are formed on the culture sheet of the substrate, and nanopillars capable of controlling the adhesiveness or migration of a cell are formed on a culture surface that serves as the bottom surface of each of the holes. The culture surface of each of the holes having a structure in which a partition wall is provided, wherein, by forming the internal nanopillars in the vicinity of the center of each of the holes, the interaction of the disseminated cells can be limited to uniform the size of the three-dimensional structures of the cells to be formed.

19 Claims, 27 Drawing Sheets

(51) Int. Cl.
*C12M 1/32* (2006.01)
*C12M 1/12* (2006.01)

(56) References Cited

U.S. PATENT DOCUMENTS

| | | | |
|---|---|---|---|
| 2006/0281172 A1* | 12/2006 | Kuwabara et al. | 435/305.2 |
| 2008/0138900 A1 | 6/2008 | Nakazawa et al. | |
| 2008/0254535 A1 | 10/2008 | Takahashi et al. | |
| 2009/0075366 A1 | 3/2009 | Tazaki et al. | |
| 2009/0298166 A1 | 12/2009 | Fang et al. | |
| 2011/0003389 A1* | 1/2011 | Nakazawa et al. | 435/383 |

FOREIGN PATENT DOCUMENTS

| | | |
|---|---|---|
| JP | 2006-122012 A | 5/2006 |
| JP | 2006-325532 A | 12/2006 |
| JP | 2008-259445 A | 10/2008 |
| KR | 10-2006-0117945 A | 11/2006 |
| WO | 2006/123570 A1 | 11/2006 |
| WO | WO 2009034927 A1 * | 3/2009 |

OTHER PUBLICATIONS

L. A. Kunz-Schughart et al., The Use of 3-D Cultures for High-Throughput Screening: The Multicellular Spheroid Model, J Biomol Screen, 9, pp. 273-285, 2004.
J. Fukuda et al., Orderly Arrangement of Hepatocyte Spheroids on a Microfabricated Chip, Tissue Eng, 11, pp. 1254-1262, 2005.
R. Takahashi et al., Formation of Hepatocyte Spheroids with Structural Polarity and Functional Bile Canaiculi Using Nanopillar Sheets, Tissue Eng., Part A, vol. 16, No. 6: 1983-1995, pp. 1983-1995, 2010.
Korean Office Action received in corresponding Korean Application No. 10-2014-7013020 dated Mar. 27, 2015.

* cited by examiner

100μm

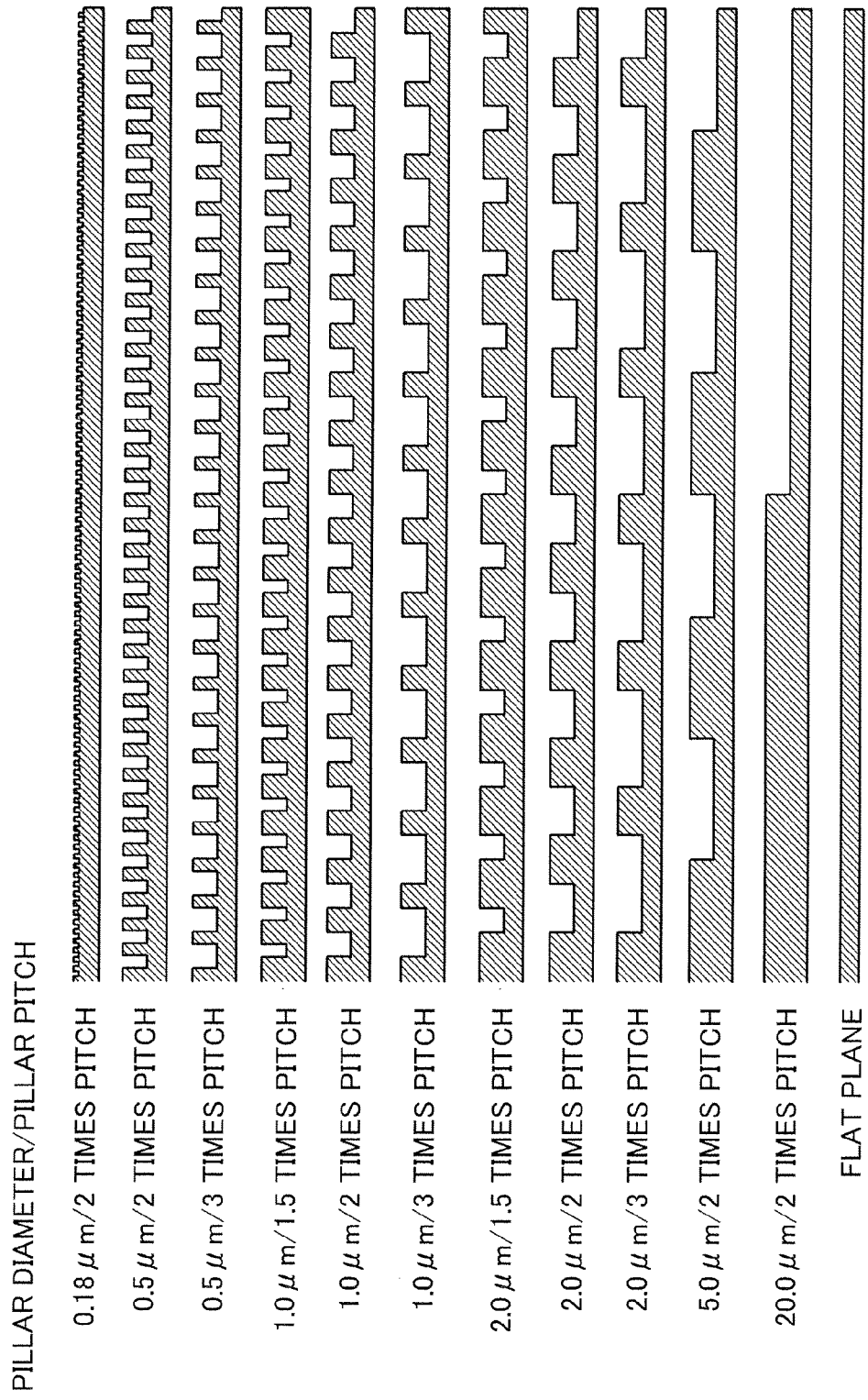

FIG. 13B
A-A, B-B PARTIAL ENLARGED VIEWS
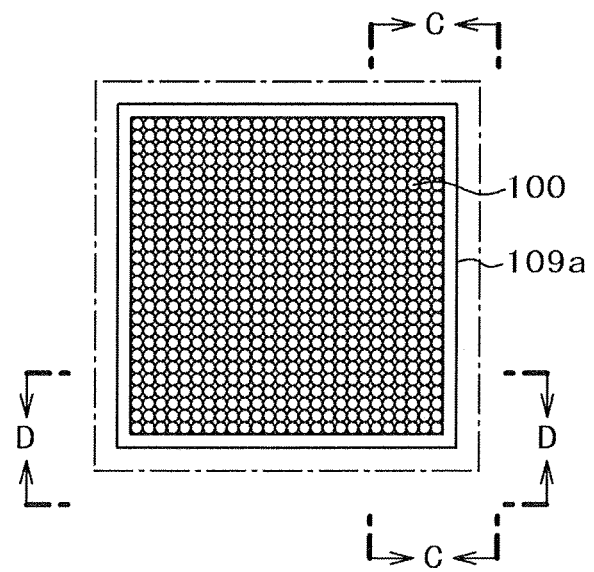
C-C, D-D PARTIAL ENLARGED VIEWS
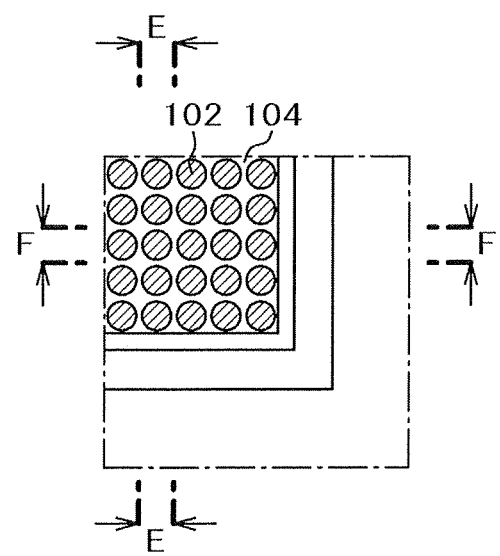

FIG. 13C
E-E, F-F PARTIAL ENLARGED VIEWS
G-G LINE END VIEW
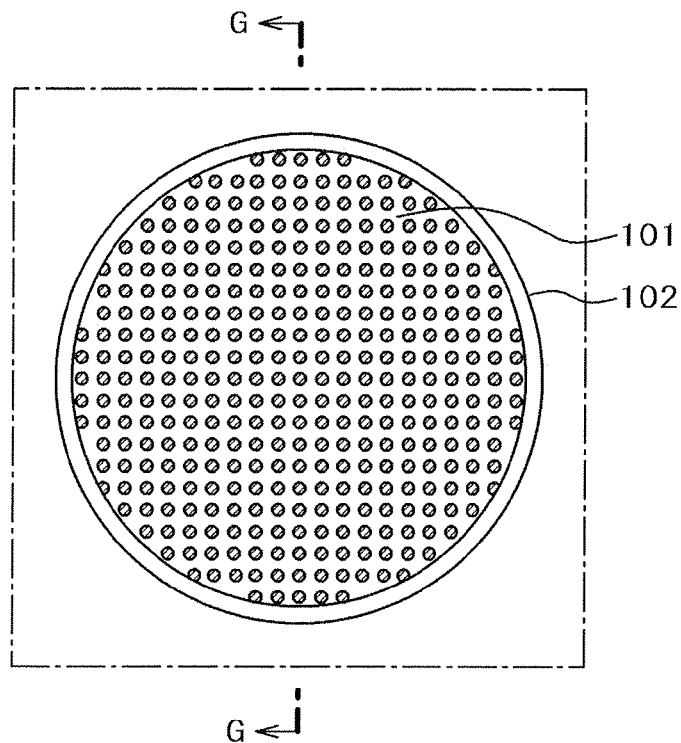
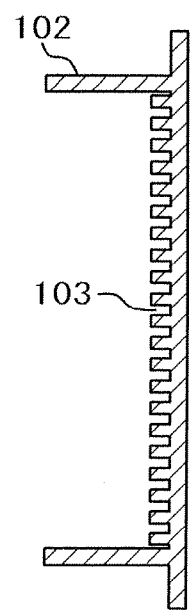

FIG. 14A
PERSPECTIVE VIEW
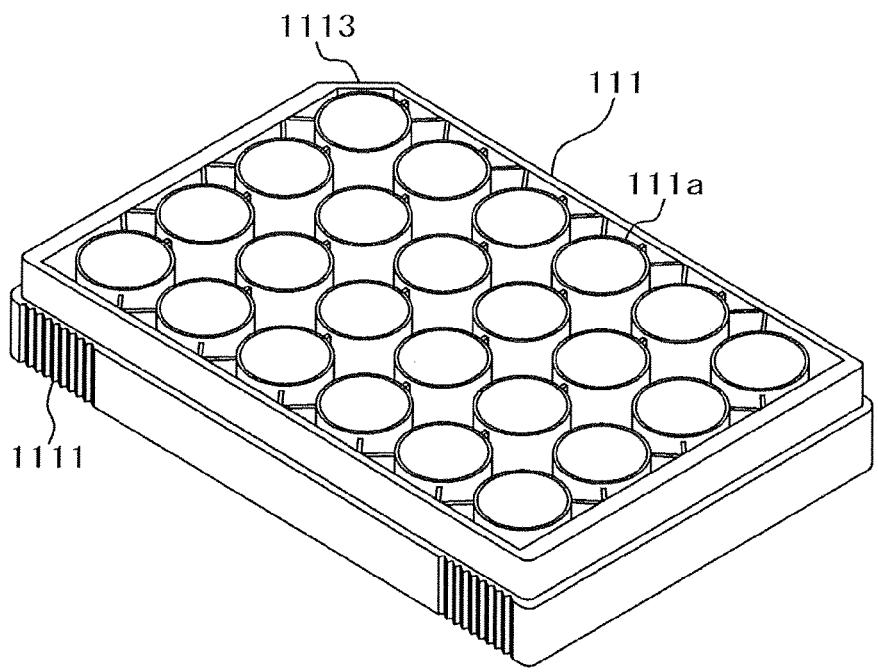
BOTTOM VIEW
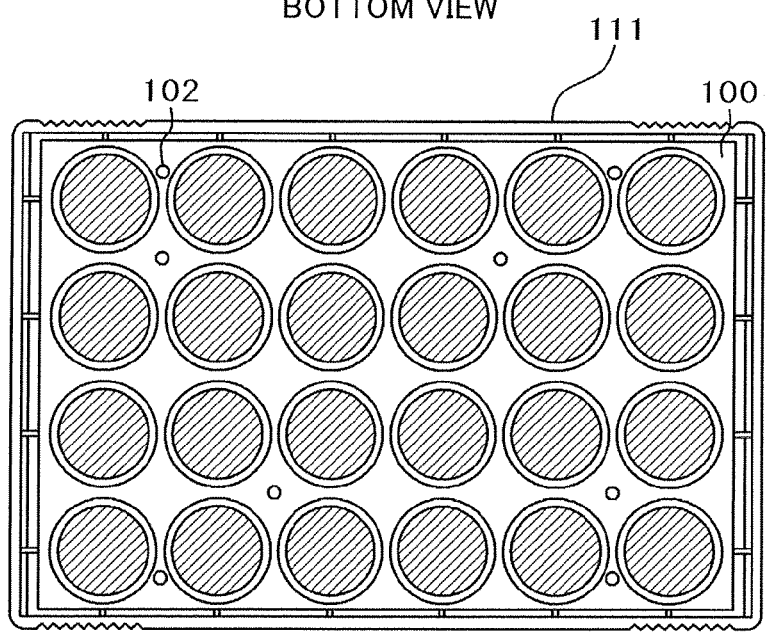

FIG. 14B
UPPER SIDE VIEW
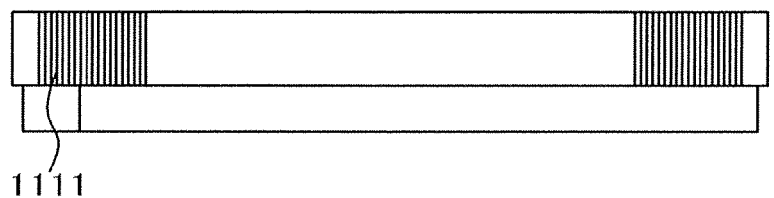
TOP VIEW
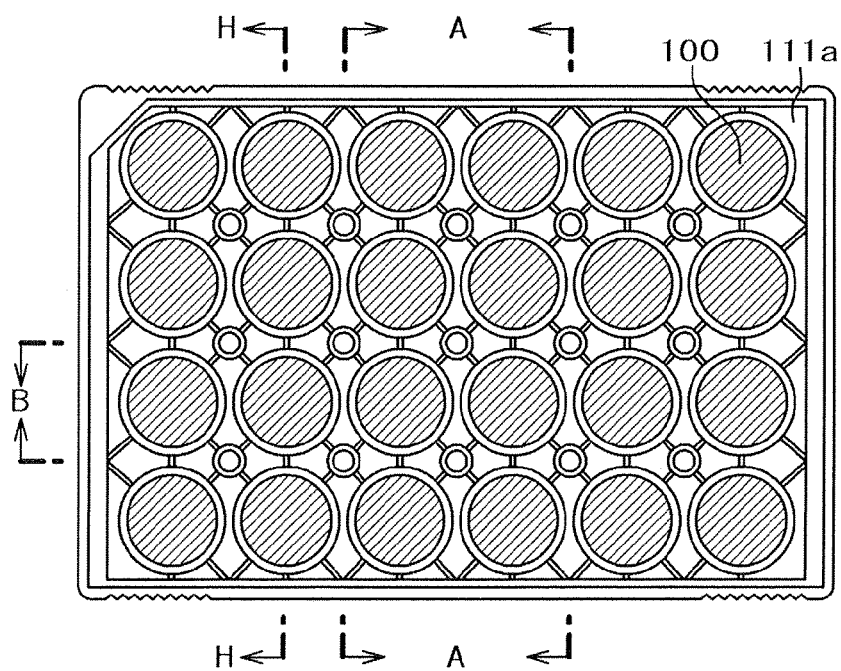
LOWER SIDE VIEW
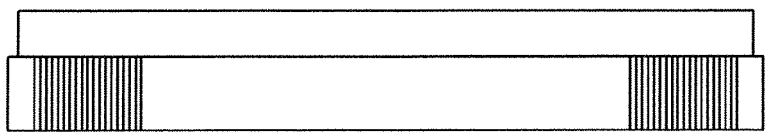

FIG. 14C
A-A, B-B PARTIAL ENLARGED VIEWS
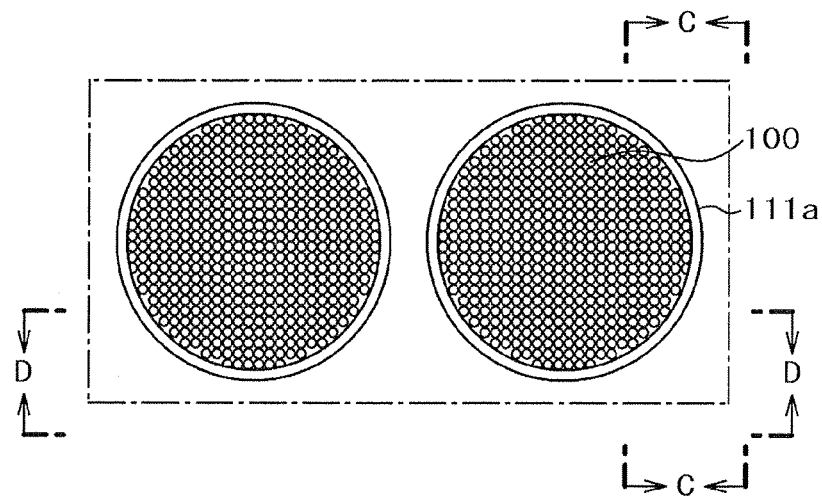
C-C, D-D PARTIAL ENLARGED VIEWS
H-H SECTIONAL VIEW
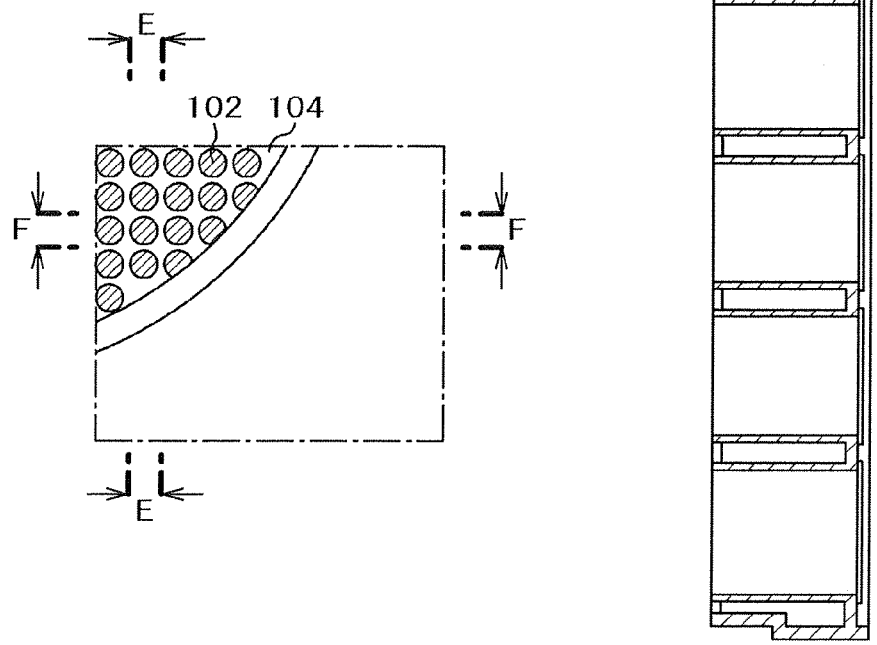

E-E, F-F PARTIAL ENLARGED VIEWS   G-G LINE END VIEW

CULTURE SUBSTRATE, CULTURE SHEET, AND CELL CULTURE METHOD

TECHNICAL FIELD

The present invention relates to technology in which, by using a culture substrate, cells of animals or plants are cultured, and globular tissues (three-dimensional tissues) and monolayer tissues (two-dimensional plain tissues) of cells are formed.

BACKGROUND ART

In developing processes of pharmaceuticals, instead of animal testing, in vitro assay using cells is desired. Particularly, it is applied more actively to screening, toxicity and metabolic testing of drug candidate materials.

Against such a background, replacing conventional animal testing, alternative approaches using cells have been tried actively, but many of them have limited capacity to predict clinical reactions. It is considered to be because, in these culture methods, cells do not have structures imitating that of the real-life systems (Non Patent Literature 1). Therefore, construction of three-dimensional tissues which fulfill functions nearer to that of real-life systems have been tried, and three-dimensional tissues of various cells have been successfully made.

As a substrate to form three-dimensional tissues of cells, a sheet for culturing on which extremely microscopic and uniform protrusions are regularly arranged (nanopillar sheet) has been developed, but it has a problem that three-dimensional tissues that have been formed have high peeling property from substrates (Patent Literature 1), and are lost during medium replacement. Also, since diameters of formed three-dimensional tissues cannot be controlled, it has a problem that the diameters are not uniform, and functions of each three-dimensional tissue vary. It remains immature for practical forming.

Accordingly, a technique to provide minute cavity structures on a culture substrate, and to form a three-dimensional tissue per the cavity (with a cellular organization micro chip) has been developed (Patent Literature 2, Non Patent Literature 2). As characters of the technique, by applying adhesive materials to the predetermined regions around the center of bottom surfaces of cavities, cell-adhered regions and cell-not-adhered regions are specified, and by rotating the cavity itself with such as a rotation drive apparatus and carrying out rotational culture, culture cells are held to near the center of bottom surfaces of cavities, cell-adhered regions.

In addition, the present inventor et al., with the aim of spheroid formation having uniform diameters, are carrying out studies of the nanopillar culture sheet (Non Patent Literature 3). The nanopillar culture sheet, by making the surface of the substrate to which cells are adhered a concavo-convex structure, is intended to control diameters of spheroids to be formed.

CITATION LIST

Patent Literature

Patent Literature 1: JP 2005-312343-A
Patent Literature 2: JP 2006-121991-A

Non Patent Literature

Non Patent Literature 1: "The use of 3-D Cultures for High-Throughput Screening: The Multicellular Spheroid Model" Leoni A. Kunz-Schughart, James P. Freyer, Ferdinand Hofstaedter, and Reinhard Ebner, J. Biomol. Screen, 9: 273-285 (2004)

Non Patent Literature 2: "Orderly arrangement of hepatocyte spheroids on a micro fabricated chip.", J. Fukuda and K. Nakazawa, Tissue Eng., 11: 1254-62 (2005)

Non Patent Literature 3: "Formation of hepatocyte spheroids with Structural Polarity and Functional Bile Canaliculi Using Nanopillar Sheets.", R. Takahashi, H. Sonoda, Y. Tabata, and A. Hisada, Tissue Eng. Part A, 1-45 (Mar. 4, 2010)

SUMMARY OF INVENTION

Technical Problem

As for cellular organization micro chips with such properties, in order to forcibly adhere cells to the specified parts on the substrate surface, chemically synthesized materials must be applied to the substrate surface and cell-adhered regions and cell-not-adhered regions must be specified, leading to some problems.

First of all, not only these applied chemical materials may have bad effects on growth of cells, but also, since this operation needs to apply or adhere chemical materials to extremely small regions, this operation becomes very troublesome work and increases the manufacturing cost.

Additionally, when disseminated cells fall into cell-not-adhered regions, they are certainly abandoned and lost with the medium at the time of medium replacement during culture, and this method is hardly an effective culturing method. Furthermore, since cells that have fallen into cell-adhered regions are forcibly caused to form tissues by rotational culture, there is fear that a stress may be placed on these cells to reduce their activeness.

Meanwhile, also in conventional nanopillar sheets, it is difficult to control cellular motions on a substrate surface, and even if it is possible to control the size and diameter of formed three-dimensional tissues, it is impossible to keep the formed three-dimensional tissues in intended places.

The objects of the present invention are to provide a culture sheet, a culture substrate, and a cell culture method using it which make it possible to form three-dimensional tissues with uniform diameters without applying chemicals to the surface of the culture substrate, and to keep the three-dimensional tissues in intended places.

Solution to Problem

In order to achieve objects described above, in the present invention, a configuration having culture regions in which a plurality of protrusions are formed, and around which partitions that terminate culture regions and being higher than the protrusions are formed, is provided.

In addition, in order to achieve objects described above, in the present invention, culturing substrates to culture cells are provided that include a culture sheet which furnished with a plurality of culture regions, and a plurality of protrusions that are formed in each of the culture region, and partitions that terminate culture regions and are higher than the protrusions, as well as with culture sheet holding sections that hold the culture sheets.

Furthermore, in order to achieve objects described above, in the present invention, as a cell culturing method using the culture substrate, a cell culturing method is provided which forms three-dimensional tissues of cells in each of the culture region, by using a culture sheet furnished with a plurality of culture regions having a plurality of protrusions inside, and having partitions higher than the protrusions formed around the culture substrate, and by disseminating cells to be cultured in each of the plurality of culture regions.

Further, in order to achieve the objects described above, in the present invention, a cell culture sheet is provided that is furnished with a plurality of culture regions, a plurality of protrusions formed in the culture regions, and partitions that terminate each of the culture region and are higher than the protrusions, and having first and second regions in each of the culture regions, the width, diameter, or pitch of the protrusion in the first region being different from that of the protrusion in the second region, and formed three-dimensional tissues being held to intended points in limited regions by partitions.

Also in addition, in order to achieve objects described above, in the present invention, a culture substrate is provided that is a culture substrate for culturing cells, furnished with a culture sheet, and a culture sheet holding section that holds the culture sheet, the culture sheet having culture regions including the first regions where a plurality of protrusions are formed and the second regions where no protrusion is formed, and forming partitions that terminate the culture regions and are higher than the protrusions.

Advantageous Effects of Invention

By applying the present invention, it is possible to form a three-dimensional tissue, using a single material only, while maintaining activeness through accelerating cell motility, which is the original function of cells, under less stressful conditions.

In addition, by integrally forming a partition of a limited area, with a single material, all cells disseminated in the limited area are to be involved in the formation of a single three-dimensional tissue. Therefore, it can be expected not only that the method is a very effective culturing method, but also that a plurality of three-dimensional tissues formed in each limited area have uniform size, are homogeneous, and are useful for cell assay.

Furthermore, it can be expected that the three-dimensional tissues are held at intended positions in a partition of a limited area. In addition, it is also possible to form two-dimensional plain tissues as required. Also as for two-dimensional plain tissues, the same effects can be expected.

BRIEF DESCRIPTION OF DRAWINGS

FIG. 9 shows views indicating various arrangement patterns of pillars in various Examples.

FIG. 13B shows the A-A and B-B parts enlarge view and the C-C and D-D parts enlarge view being the partial enlarged views of the culture substrate in Example 1.

FIG. 13C shows the E-E and F-F parts enlarge view, and the G-G line end view, being the partial enlarged view and the end view of the culture substrate in Example 1.

FIG. 14A shows the external perspective view and the bottom view of the culture substrate in Example 2.

FIG. 14B shows top view, upper and lower side views of the culture substrate in Example 2.

FIG. 14C shows the A-A and B-B parts enlarge view, and the H-H sectional view, being the partial enlarged view and the partial sectional view of the culture substrate in Example 2.

DESCRIPTION OF EMBODIMENTS

Hereinafter, the best mode for culturing cells by using the culture sheet, realizing the forming method of three-dimensional tissues being lumps of cells or two-dimensional plain tissues, by using drawings, is explained in detail.

Example 1

In Example 1, a case in which the culture sheet is applied to a chamber slide being a culture sheet holding member is shown. Hereinafter, unlike conventional nanopillar sheets, a sheet in the present invention that has a partition structure forming the culture region, and in the partition structure a plurality of protrusions are formed, is referred to as a culture sheet. The culture sheet is made with materials without bad effects on cells, in this example, polystyrene is used. However, needless to say, the material is not limited to polystyrene.

Figure 1:
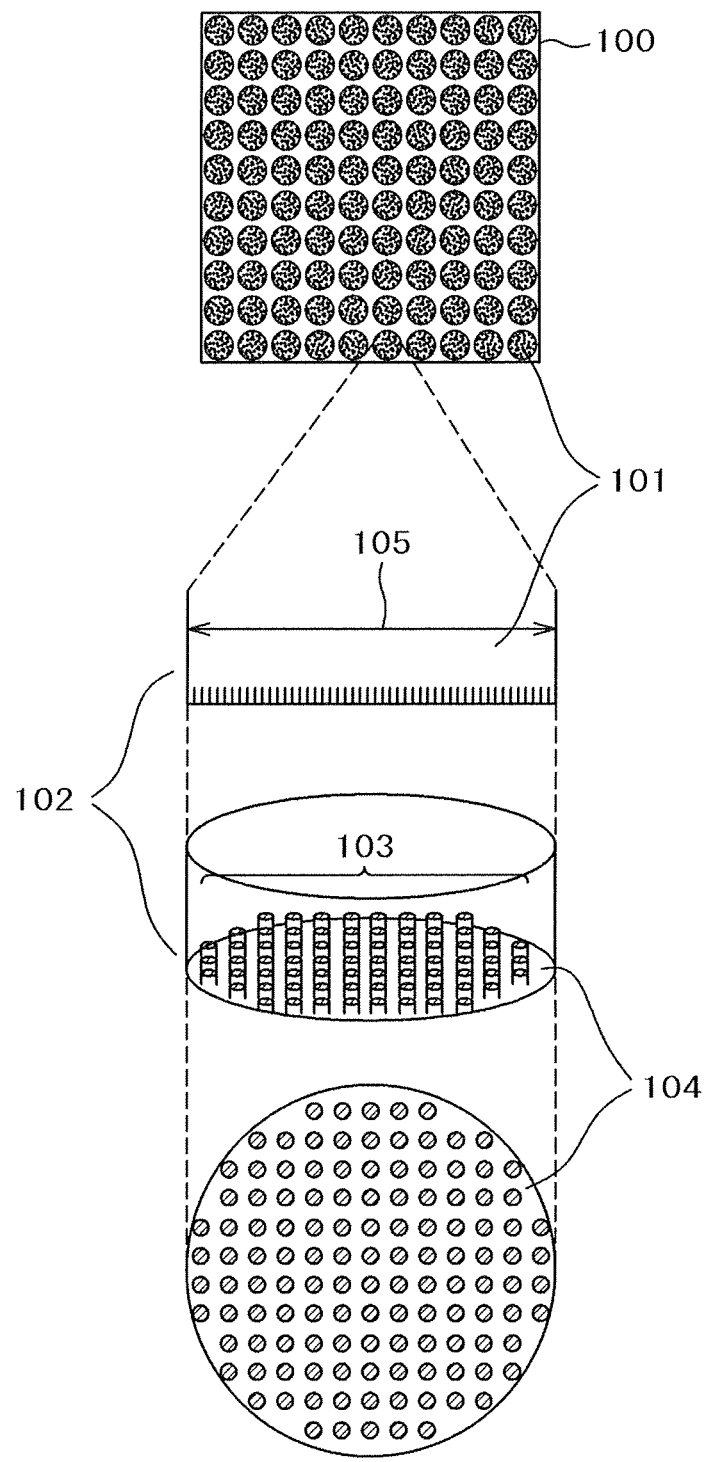
FIG. 1 is a view showing the culture sheet and the hole structure in the culture sheet in regard to Example 1.

FIG. 1 is a diagram of a scanning electro microscope photograph of the culture sheet 100 made in Example 1. Also at the same time, FIG. 1 shows a structure of the holes 101 constituted by partition structures 102 (hereinafter referred to as hole) a plurality of which existing per a culture sheet. Inside of the holes 101 constitutes a culture region being a cell tissue forming unit.

A plurality of protrusions 102 held on the bottom face of the holes 101 are comprised of a plurality of micro protrusions 103 (hereinafter, may be referred to as protrusions, pillars, or nanopillars). In addition, the diameters of the holes 101 are referred to as the hole diameters 105. In the culture sheet 100, the holes 101 furnished with the partition walls 102 described above, and a plurality of protrusions 103 formed in the holes 101 are integrally formed with the same material. Furthermore, the holes 101 are not limited to be round-shaped, but may be square-shaped or others.

As described above, since the holes 101 furnished with the partition walls 102 and a plurality of protrusions 103 formed in the holes 101 are integrally formed with a single material without bad influence on cells as the culture sheet 100, in the culture steps, cells can be grown without adhesions of foreign substances to cells. Additionally, since cells grow in each of the partition, forming cells of the uniform size becomes possible.

Also, since a plurality of protrusions are furnished in the surroundingly placed partition walls 102, cell motility originally held by cells is promoted, cells grow by the motility, and cell culture keeping activeness and without influence of disturbance (stress) by such as rotational culture becomes possible.

Trying to form the culture regions with the holes 101 and the protrusion assemblies 103 as separate bodies requires jointing of them by adhesion or deposition is required.

For example, if they are jointed by adhesion, adhesive ingredients may be mixed into the culture regions, and have negative influences on produced cells. Also, in cases of deposition jointing, since inner diameters of holes 101 are diameters of extremely small regions at the cell forming level, it is considerably difficult to deposit with forming the object cell regions without damaging the partitions and protrusions. If the partitions and protrusions are damaged or deformed, needless stress may be added or cell motility itself may be disturbed in the cell forming steps.

Accordingly, it is desirable that the hole bottom surfaces 104, partition walls 102, and protrusions 103 to constitute holes 101 forming culture regions are integrally formed. Thus integral formation makes carrying out of culture with elimination of unneeded ingredients other than needed ingredients for cell culture possible, and is suitable.

Figure 2:
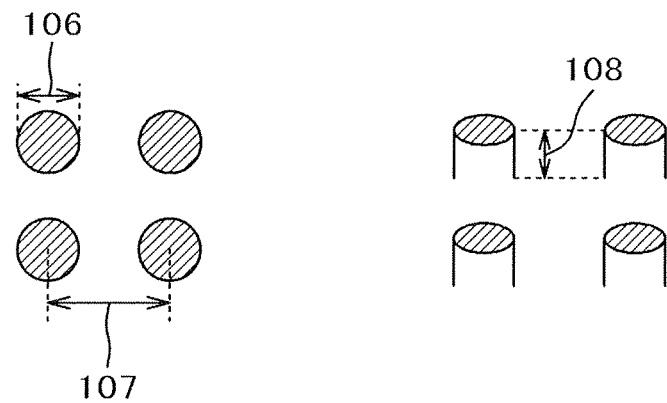
FIG. 2 shows views indicating the nanopillar structure in regard to Example 1.

Next, enlarged views of protrusions 103 are shown in FIG. 2. A pillar diameter (106 in FIG. 2) indicates the diameter of the tip section of the protrusion. A pillar pitch (107 in FIG. 2) indicates the distance from the center of the tip section of the protrusion to the center of the neighboring tip section of the protrusion. A pillar height (108 in FIG. 2) indicates the height from the tip section to the bottom section of the protrusion.

In the present example, the pillar diameter, pillar pitch, and pillar height of the culture sheet are 2.0 µm, 4.0 µm, and 1.0 µm, respectively, however, as described later, other culture sheets may also be used. In the present example, the height of the partition structure is 70 µm, but, the height is not limited to the value, and may be suitably on the level that cells to be formed cannot get over.

The culture sheet 100 in the present example is manufactured by the method described later.

A polystyrene film with thickness of 400 µm was pressed with a mold in which circular holes with diameter of 200 µm and depth of 70 µm are placed in a square shape, and on the bottom surface, micro holes with diameter of 2.0 µm and depth of 1.0 µm are formed at the pitch of 4.0 µm, at 135° C. with pressure of 2 MPa. After cooling to room temperature, by taking the set out from the press equipment, and peeling off the polystyrene film from the mold, a culture sheet holding a plurality of holes with the hole diameter of 200 µm and having a plurality of protrusions on the bottom surface can be manufactured.

In the present example, the mold material is a silicone wafer, and in order to prevent adhesion of the mold and the polystyrene film during the culture sheet manufacturing, the mold is preliminarily given a mold releasing treatment with a fluorine mold releasing agent. In the present example, the mold material is a silicone wafer, however, molds made of such as metal materials may also be used.

Figure 3:
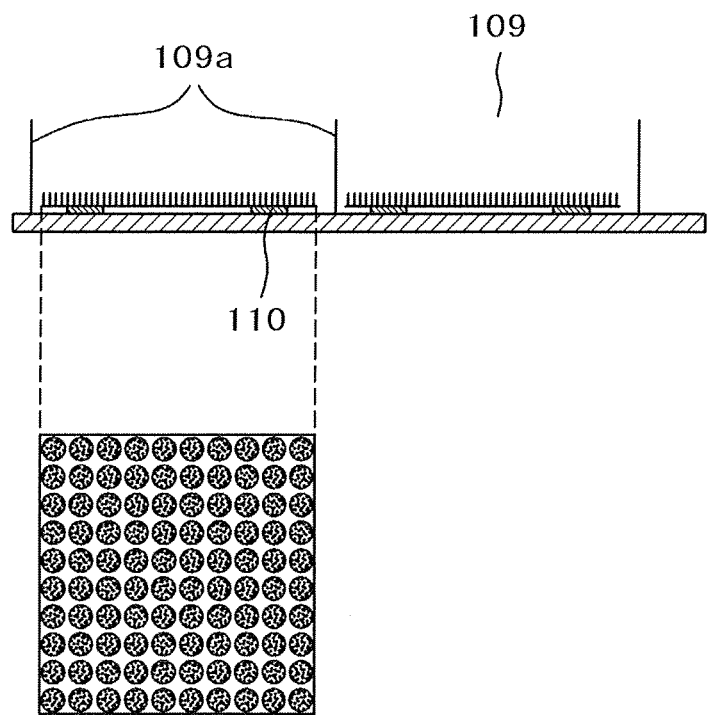
FIG. 3 is a view showing the chamber slide applied by a culture sheet in regard to Example 1.

As shown in FIG. 3, by cutting the culture sheet 100 thus manufactured by integral molding with the single material into 2 cm square, applying a surgical adhesive 110 to the glass bottom surface of the chamber slide 109 and bonding the culture sheet 100, a chamber slide 109 applied with the culture sheet 100 is manufactured. Meanwhile, in FIG. 3, 109a indicates frames separating each part of the culture sheet 100. This frame 109a is formed, for example, with plastic materials. In addition, the shape of the frame such as 109a is not limited to square shape, and may be round shape and other shapes.

Figure 13A:
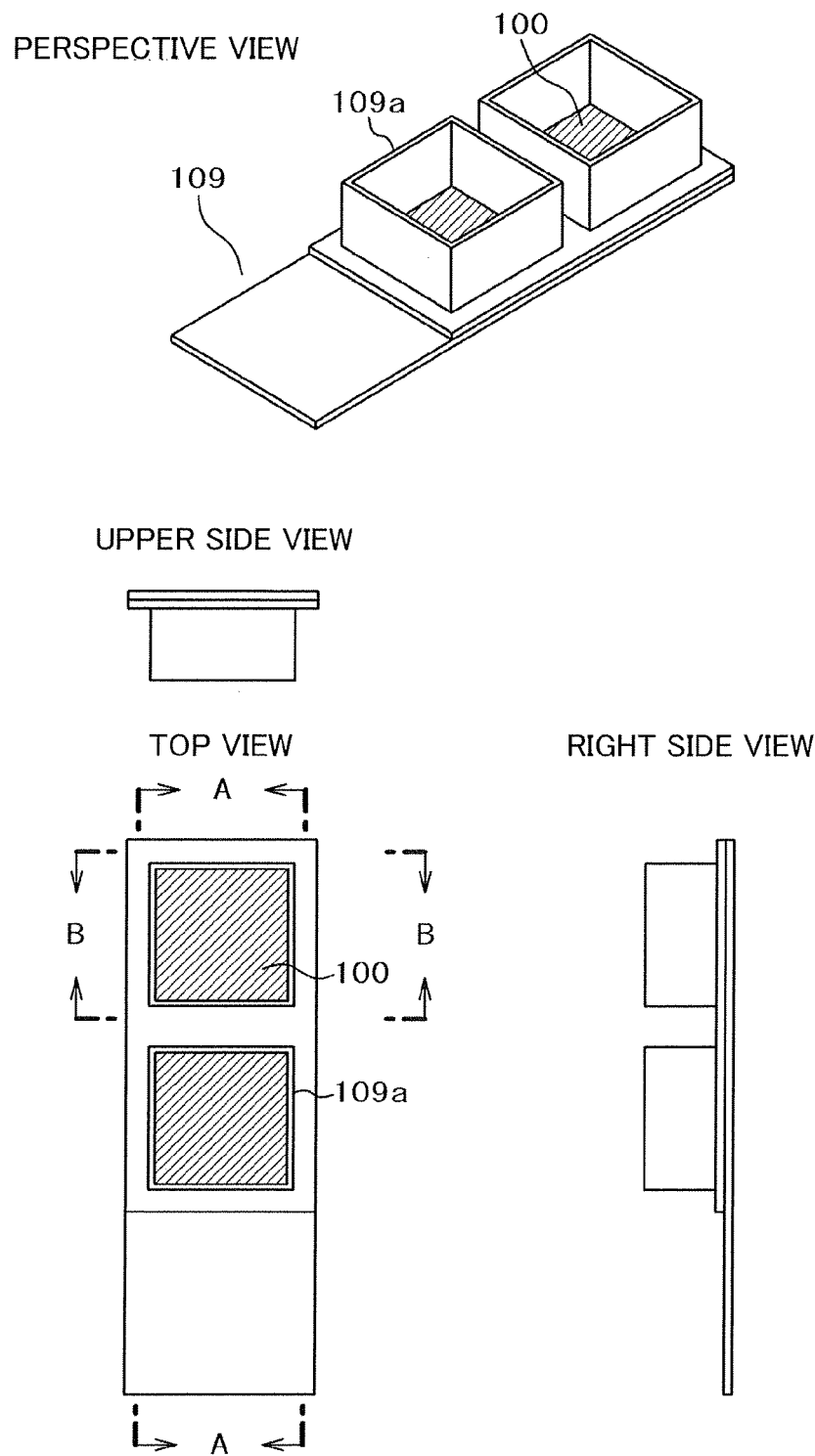
FIG. 13A shows external perspective view, top view, upper and lower side views of the culture substrate in Example 1.
Figure 14D:
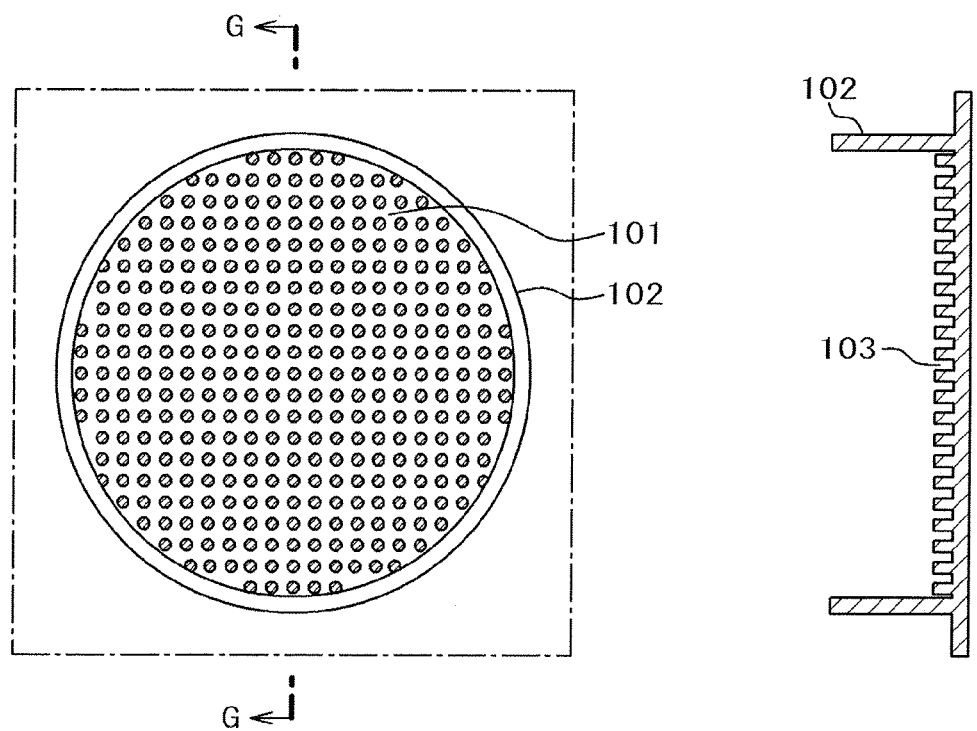
FIG. 14D shows the E-E and F-F parts enlarge view, and the G-G line end view, being the partial enlarged view and the end view of the culture substrate in Example 2.

In FIGS. 13A to 13C, a total configuration view and sectional views of chief parts of the chamber slide adhered by the culture sheet of the present example are shown.

FIG. 13A shows an external perspective view, a top view, and upper and lower side views of the culture substrate in the present example. As for right and left side views, since their morphologies are apparent from the perspective view, their indication is omitted.

FIG. 13B shows partial enlarged views, and indicates the A-A and B-B parts enlarge view and the C-C and D-D parts enlarge view.

FIG. 13C shows a partial enlarged view and an end view, and indicates the E-E and F-F parts enlarge view and the G-G line end view.

The material shown in FIGS. 13A to 13C is a culture substrate (culture container) to culture human cells or cells of animals or plants. It includes a culture sheet 100 and a holding section (chamber slide) 109, and on the surface of the culture sheet 100, a plurality of partition sections 102 are formed and furnished on inner bottom surface of cylindrical hole parts 109a formed in the holding section 109.

Furthermore, inside of each of the partition section, the culture region having a plurality of micro protrusions 103 is formed. If the object cells to be cultured are added into the hole parts 109a so as to be added to the sheet plane constituting the culture region in partition sections 102, they are held by a plurality of micro protrusions 103, and the object cells are cultured.

Example 2

Figure 4:
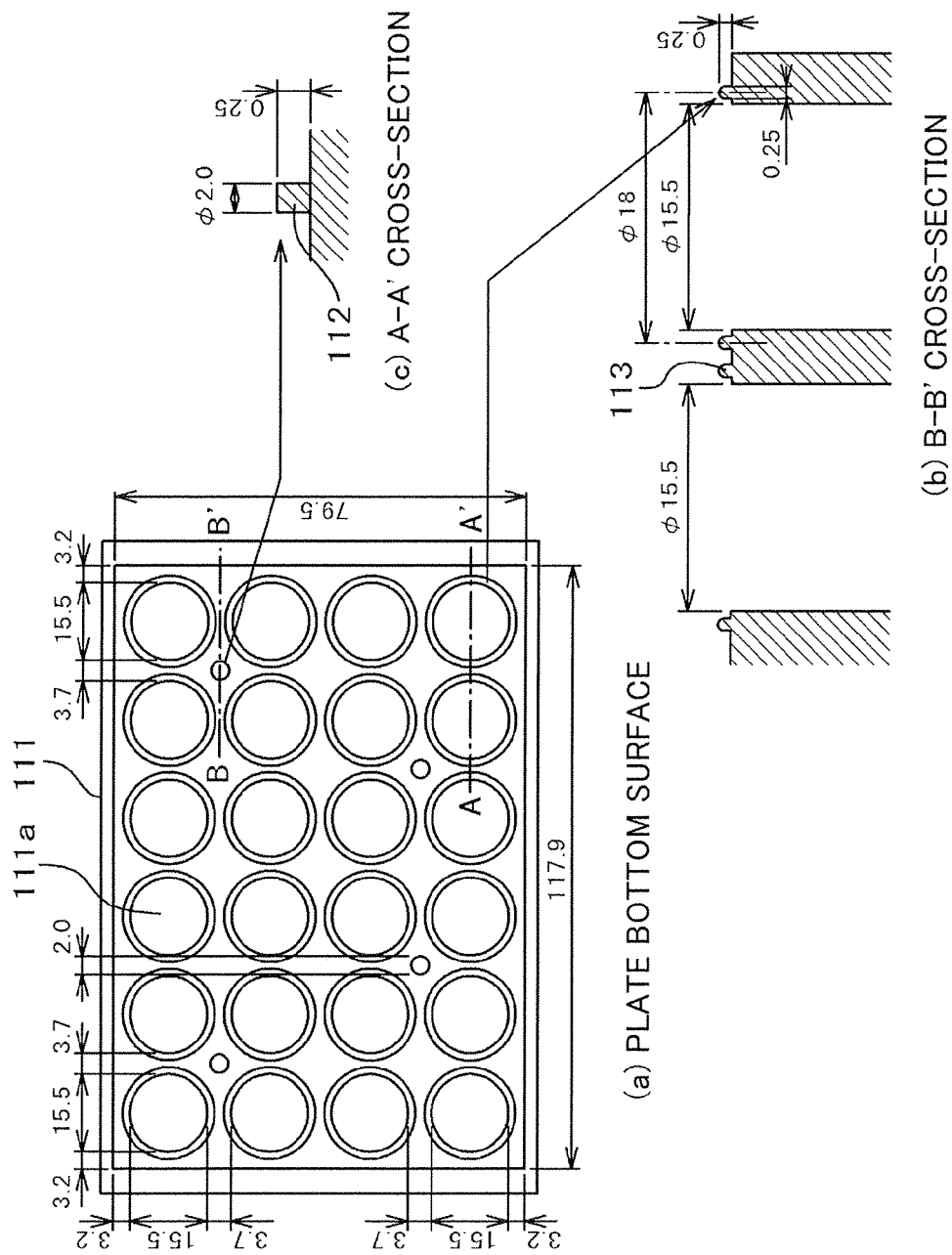
FIG. 4 shows views indicating the configuration of the plate frame in regard to Example 2.
Figure 5:
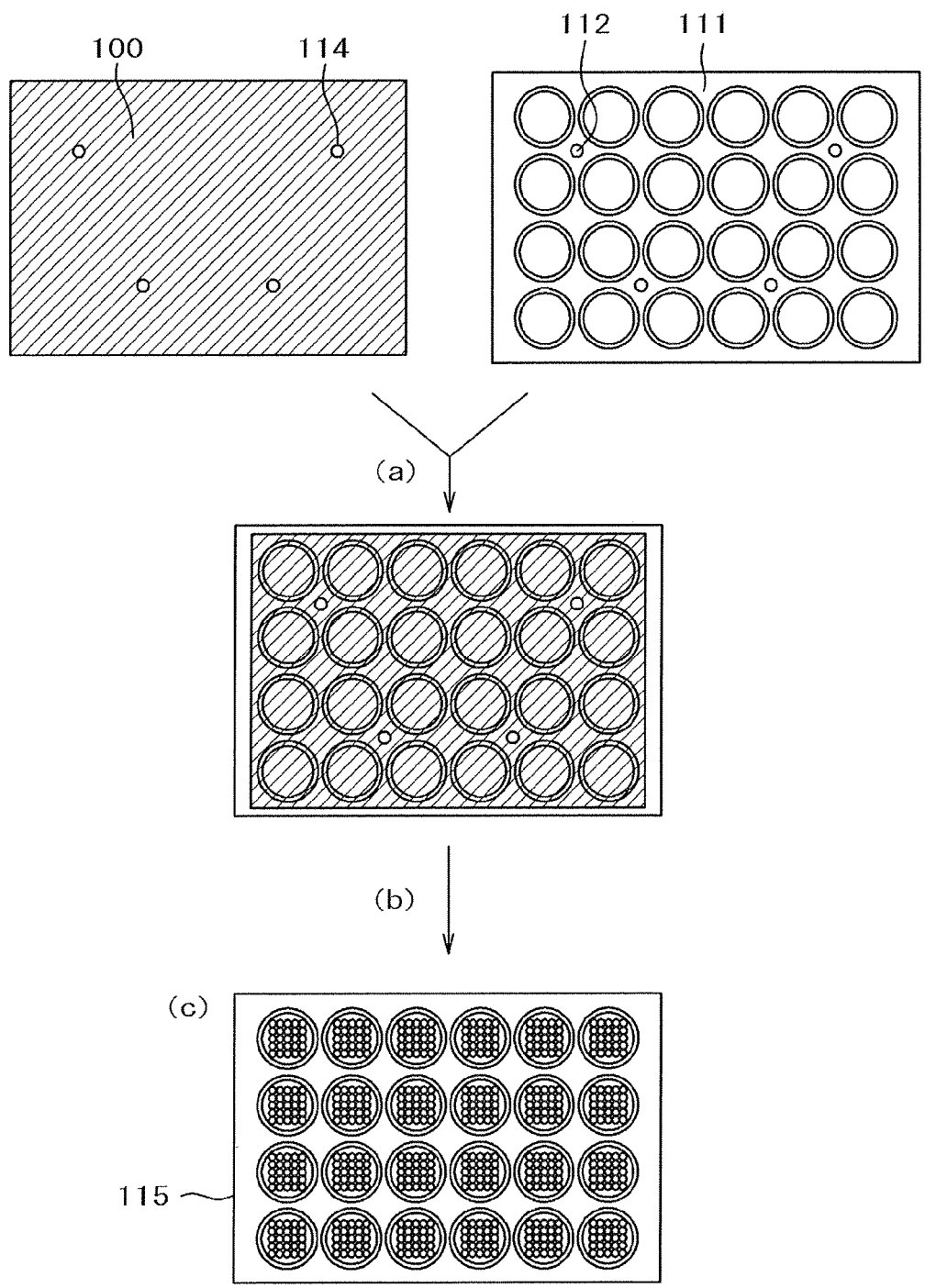
FIG. 5 shows views to explain the flow of ultrasonic deposition between the plate and the culture sheet in regard to Example 2.

Next, according to FIG. 4 and FIG. 5, the second example is explained. In Example 2, the constitution of a multi-well plate with a culture sheet, and its manufacturing example are shown. FIG. 4(a) is the bottom view of the frame 111 constituting a multi-well plate. In the frame 111 being the holding material of the culture sheet, in the surface space of about 125 mm wide and about 80 mm long and about 20 mm high, four holes in a vertical row and 6 holes in a horizontal row, totally 24 cylindrical holes 111a are molded. As the material, polystyrene is used.

The number of holes formed in the frame is normally from 6 to 1536. Since the number is changed depending on the application, also in the case of this frame, the number of holes is not limited to 24. In addition, the material of the frame is not limited to polystyrene.

In manufacturing of the culture substrate, the frame 111 and a culture sheet 100 are jointed with ultrasound deposition.

The frame is preliminarily treated as follows. First, in order to prevent misaligning the cell culture sheet and the plate by ultrasonic vibration given during deposition of the frame 111 and a culture sheet 100, protrusions for film fixing 112 are processed on the bottom surface of the frame 111. Second, in order to deposit the culture sheet with ultrasound, rib structure 113 is furnished.

FIGS. 4(b) and 4(c) indicate A-A', B-B' sectional views of FIG. 4(a), respectively. Additionally, in order to fit the protrusions for film fixing to the same positions when the frame and the culture sheet are piled, holes with the same diameter 114 are preliminarily provided in the culture sheet. Then, the frame and the culture sheet 100 are jointed with ultrasound deposition.

The process is shown in FIG. 5. First of all, the protrusions for film fixing of the frame and the holes of the culture sheet are combined, and the frame and the culture sheet are piled (FIG. 5(a)). Next, ultrasound is generated by an ultrasonic oscillator and launched through a converter, a booster, and a horn from the culture sheet side, and the frame and the culture sheet are deposited (FIG. 5(b)). A horn is an apparatus which exposes suitable positions with ultrasound having suitable energy. A dedicated device designed to appropriately generate ultrasound according the position of the rib structure was manufactured and used. 115 indicated the top view of the thus manufactured plate.

In the present example, by using ultrasonic deposition, the frame and the culture sheet was jointed, however, needless to say, the jointing method is not limited to this method. Since ultrasonic deposition can realize plate manufacturing without intervention of organic substances such as adhesives which give influences on cells, it is needless to say that the obtained culture sheet has no bad influence on cells, and applicable to not only toxicity tests and metabolic tests in new drug development process but also to tissue formation for regenerative medicine, and is useful.

Furthermore, it is needless to say, also in the chamber slide-shaped culture substrate of FIG. 3 exemplified in Example 1, by furnishing a plurality of rib structures on the bottom of the frame 109a, and by using the rib structures, deposition of the culture sheet 100 is performed, a culture substrate can be made by the same method as that of the present example.

In the thus manufactured culture substrates, and in the culture sheet 100 formed on the bottom surface of the frame 111, a plurality of holes 101 are formed, and a plurality of protrusions composed on the hole bottoms 104 are comprised of a plurality of micro protrusions 103 (hereinafter referred to as protrusions, pillars, or nanopillars). In addition, the diameters of the holes 101 are referred to as the hole diameters 105. In the culture sheet 100, the holes 101 furnished with partition walls 102 described above and a plurality of protrusions 103 formed in the holes 101 are integrally formed with the same material. Furthermore, the holes 101 are not limited to round shapes, and may be other shapes such as square shapes.

As described above, since the holes 101 furnished with the partition walls 102 and a plurality of protrusions 103 formed in the holes 101 are integrally formed with a single material without bad influence on cells as the culture sheet, in the culture steps, cells can be grown without adhesions of foreign substances to cells.

Additionally, since cells grow in each of the partition, forming cells with the uniform size becomes possible.

Also, since a plurality of protrusions are furnished in the surroundingly placed partition, cell motility originally held by cells is promoted, cells grow by the motility, and cell culture with activeness kept and without influence of disturbance (stress) by such as rotational culture becomes possible.

If the culture regions are tried to be formed, with the holes 101 and the protrusion assemblies 103 as separate bodies, jointing of them by adhesion or deposition is required. For example, if they are jointed by adhesion, adhesive ingredients may be mixed into the culture regions, and have negative influences on produced cells.

Also, in cases of deposition jointing, since inner diameters of holes 101 are diameters of extremely small regions at the cell forming level, it is considerably difficult to deposit with forming the object cell regions without damaging the partitions and protrusions. If the partitions and protrusions are damaged or deformed, in the cell forming steps, needless stress may be added or cell motility itself may be disturbed.

Accordingly, it is desirable that the hole bottom surfaces 104, partition walls 102, and protrusions 103 to constitute holes 101 forming culture regions are integrally formed. Thus integral formation makes carrying out of culture with elimination of influences of unneeded ingredients other than needed ingredients for cell culture possible, and is suitable.

In FIGS. 14A to 14D, a total configuration view and sectional views of chief parts of the multi-well plate with the culture sheet of the present example are shown.

FIG. 14A shows an external perspective view and a bottom view of the culture substrate in the present example.

FIG. 14B shows a top view, and upper and lower side views of the culture substrate. As for right and left side views, since their morphologies are apparent from the external perspective view, their indication is omitted.

FIG. 14C shows partial enlarged views and a partial sectional view, and indicates the A-A and B-B parts enlarge view, the C-C and D-D parts enlarge view, and the H-H line sectional view.

FIG. 4D shows a partial enlarged view and an end view, and indicates the E-E and F-F parts enlarge view, and the G-G line end view.

The material shown in FIG. 14A-FIG. 14D is a culture substrate (culture container) to culture human cells or cells of animals or plants, and includes a culture sheet 100 and a holding section (frame) 111 to hold the culture sheet 100.

On the surface of the culture sheet 100, a plurality of holes 101 are formed and are furnished on inner bottom surface of cylindrical hole parts 111a formed in the holding section.

Furthermore, inside of each of the partition section, the culture region having a plurality of micro protrusions 103 is formed. If the object cells to be cultured are added into the hole parts 111a so as to be added to the sheet plane constituting the culture region in holes 101, they are held by a plurality of micro protrusions 103, and the object cells are cultured.

In addition, the culture substrate in this example shows a case in which a culture sheet is deposited from the back surface of the frame 111, the frame 111 being the holding part and the culture sheet 100 are deposited through jointing parts 1112.

The jointing parts 1112 are furnished outside of holes 111a, and culture regions are not influenced by the deposition.

Accordingly, deposition is exemplified in this example, but the jointing method is not limited to deposition. Since by other jointing methods, the culture regions are not influenced, adopting other jointing methods is also possible.

Furthermore, as for the substance in the present example, the frame 111 has a square shape, and among its four apexes, at least one is cut. The formation of the cut plane 1113 has an effect to make identifying the holes of the substrate for workers to culture easier.

It is needless to say that the cut plane is not indispensable, and there may not be any. Also, in the culture substrate, anti-slips 1111 are furnished, and they can prevent sudden fluctuation or falling of the substrate by workers during working.

Example 3

In Example 3, an applying example of cells to tissue cells with using the culture substrates manufactured in Example 1 and Example 2 is shown. In development of new drugs, construction of a three-dimensional tissue which reflects vital functions has demands from various evaluations using cells as alternatives to animal experiments.

In addition, since three-dimensional tissues must be formed before culturing induced pluripotent stem cells (iPS cells) and embryonic stem cells (ES cells) and differentiating to object cells, also in regenerative medicine, a technology which easily constructs three-dimensional tissues has been demanded. Against such backdrop, an example to form three-dimensional tissues by especially using chamber slides is shown here. However, even if multi-well plates are used, essential parts of cell culturing are the same. In the present example, a case using rat liver cells is shown, but as described above, the present invention is applicable to various animal or plant cell species, and is not specifically limited to cell species.

Preparation of Liver Cells is Performed Following the in situ collagenase perfusion technique. Details are as follows. Under anesthesia with pentobarbital, the abdominal cavities of Fisher 344 male rats (7 to 10 weeks old) are opened, then a catheter is inserted into the portal vein, and a pre-perfusion solution (Hank's balanced salt solution including EGTA not including $Ca^{2+}$ and $Mg^{2+}$) is injected.

At the same time, the inferior vena cava in the lower liver is incised, and blood is ejected. Next, the thoracic cavities are opened, the inferior vena cava entering the right atrium is incised, and the inferior vena cava in the lower liver is stopped with forceps, and perfusion is performed. After confirming that blood removal from the liver has been sufficient, the perfusion of the pre-perfusion solution is stopped. The perfusion solution is changed into the collagenase solution, and perfusion is performed.

In the present example, perfusion is performed using the Hank's balanced salt solution including 0.05% collagenase, but the perfusion solution is not limited to the solution. After confirming that intercellular tissues have been digested with collagenase, perfusion is stopped. The liver is cut off, is cut into thin strips in the cooled Hank's balanced salt solution, and is dispersed to a cellular level by pipetting. Then, with gauze filtration, undigested tissues are removed. Centrifugal separation of the cellular suspension with conditions of 50 G and a minute is repeated a few times, and non-parenchymal cells are removed. Then, by using the isotonic Percoll solution, with centrifugal separation with conditions of 500 G and five minutes, damaged liver cells are removed. The survival rate of the obtained liver cells is measured with trypan blue-exclusion method, and cells having the survival rate of 85% or more are used for culturing. In the present example, cells having the survival rate of 85% or more are used for culturing, but it is needless to say that the survival rate must not be limited to 85%. Furthermore, preparation of liver cells is not necessarily limited to the in situ collagenase perfusion technique.

The culturing flow chart of liver cells thus obtained is shown in FIGS. 6A-6E.

Figure 6A:
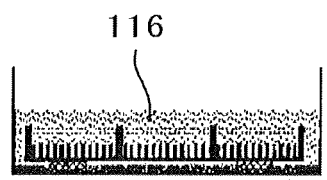
FIGS. 6A-6E show views indicating the flow chart of liver cell culturing in regard to Example 3.
Figure 6B:
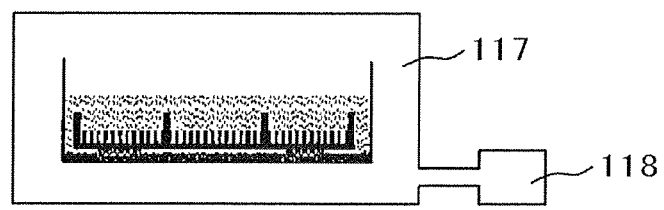
Figure 6C:
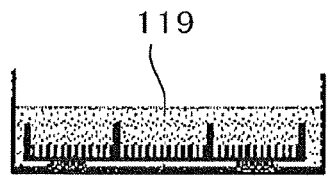

In the flow of FIGS. 6A-6E, first of all, to the chamber slide-type culture sheet manufactured in Example 1, type I collagen 116 is applied. 1 to 1.5 mL of the diluted solution made by dilution of the type I collagen weak acidic solution to the predetermined concentration with sterilized water is added to the chamber slide described above (FIG. 6A). Next, in order to make the added type I collagen completely absorbed to the nanopillar sheet 100, pressure reduction operation is performed (FIG. 6B). The pressure reduction operation is performed by using a pressure reduction container 117 and a pressure reduction pump 118, at 0.04 atmospheric pressure or lower. The pressure reduction time is not specifically limited, but in the present example, it is 10 minutes. The device configuration used for pressure reduction is not specifically limited. In the present example, the range of the predetermined concentration of the diluted solution is 100 ng/mL or more, and 10 μg/mL or less. The concentration is not necessarily limited to the predetermined range, but the range is the suitable range in which spherical three-dimensional tissues are formed. Lastly, redundant type I collagen is removed, phosphate buffered saline (PBS) (–) 119 is added (FIG. 6C). This operation is performed three times, and redundant type I collagen is washed out.

Figure 6D:
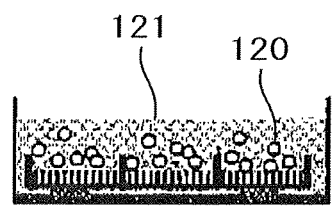

Liver cells 120 prepared with the in situ collagenase perfusion technique, as described above, is suspended in the media 121, and are disseminated to the NP sheet to which the prepared type I collagen in the same way as describe above is applied (FIG. 6D). The medium is not especially limited, but William's medium E including a medium including serum (fetal calf serum (FCS)), insulin, and dexamethasone (hereinafter referred to as a medium (including 10% FCS)) is used. In the present example, William's medium E especially including 10% FCS, 8.6 nM insulin, and 255 nM dexamethasone is used. After dissemination, by using a $CO_2$ incubator, under conditions of 5% $CO_2$, 37° C., culturing is started, and after 18 hours or more has passed, the first medium replacement is performed, and then, medium replacement is performed every 24 hours. The medium used for culture after 18 hours or more of dissemination is not specially limited, but in the present example, a medium in which FCS is removed from the medium (including 10% FCS) (hereinafter, referred to as medium (not including FCS)) is used.

Additionally, the disseminating density of liver cells in the present example is $1\times10^5$ cells/mL, but the density is not necessarily limited to this value. In the present example, the pillar diameter, pillar pitch, and pillar height of the culture sheet 100 used for culturing are 1.0 μm, 2.0 μm, and 4.0 μm, respectively, however, they are not limited to these values.

Figure 6E:
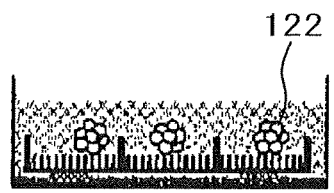

In addition, the concentration of the type I collagen added to the culture sheet in the present example is 100 ng/mL, but other concentrations may be used. Depending on cellular conditions, even if the concentration is another, a spheroid may be formed. After totally 96 hours of culturing, three-dimensional tissues 122 are formed (FIG. 6E). A photograph indicating the results of actual culturing of liver cells by using the culture sheet described above having the hole diameter of 200 μm is shown in FIG. 7.

Figure 7:
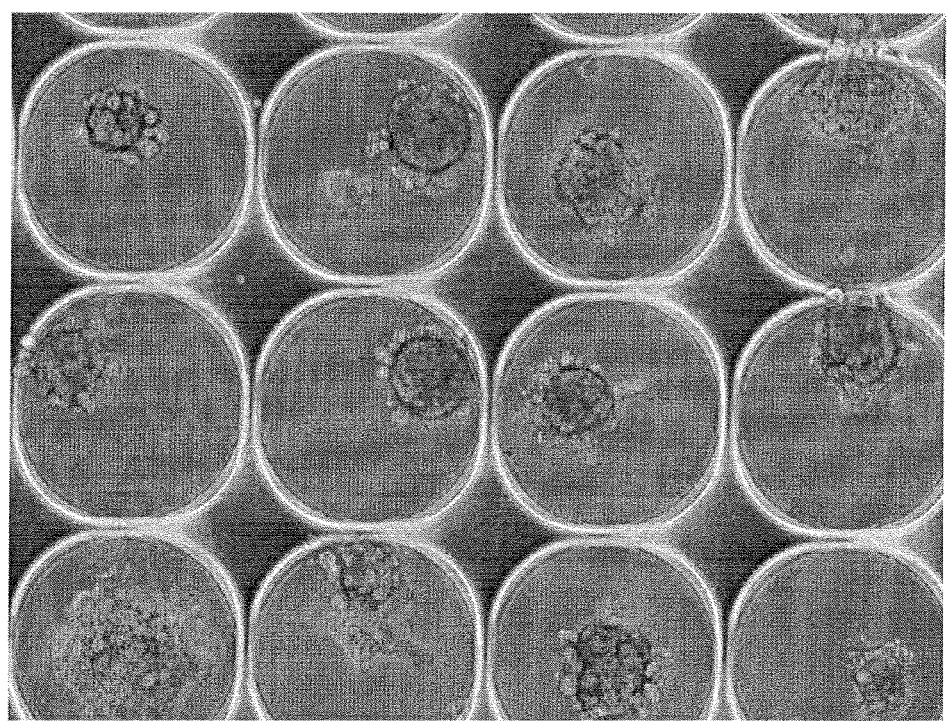
FIG. 7 is a view showing the photogram of the liver cell three-dimensional tissues according to the liver cell culturing flow with the culture sheet in regard to Example 3.

As is obvious from FIG. 7, even without application of special chemical substances to the surface of the culture sheet and through static culture giving less stress to the cells, spherical three-dimensional tissues with such a uniform size were formed. Since this method is considered not to eliminate the cellular activity originally held, and is an effective culturing method for such as cell assay.

Example 4

Figure 8A:
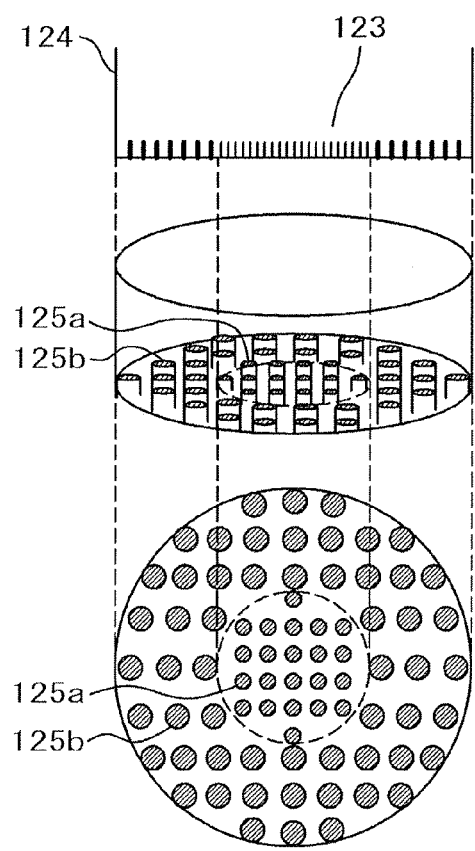
FIGS. 8A-8D show views indicating the two-stage, multi-stage nanopillar culture sheets in regard to Example 4.
Figure 8B:
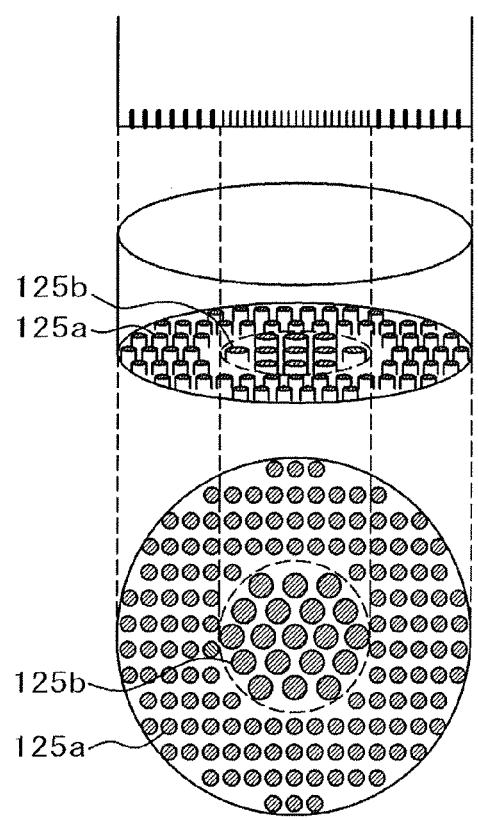

In FIGS. 8A-8D, as Example 4, modifications of the examples of the culture sheet 100 described above are shown. First of all, the culture sheet 123 indicates a case in which, as shown in FIG. 8A, by placing arranging patterns of protrusions which bring differences in cellular migration and adhesiveness, in two stages, the first arranging pattern 125a and the second arranging pattern 125b surrounding the first pattern, on the first arranging pattern 125a (for example, near the center of the hole), a three-dimensional tissue or a two-dimensional plain tissue is formed.

And conversely, the culture sheet 123 indicates a case in which, as shown in FIG. 6B, by placing the second arranging pattern 125b and the first arranging pattern 125a surrounding the second pattern in two stages, on the second arranging pattern 125b (for example, hole peripheral zone), a three-dimensional tissue or a two-dimensional plain tissue is formed. Furthermore, 124, similarly in the previous Example, shows holes. Dashed lines show the boundary of the two patterns.

Figure 8C:
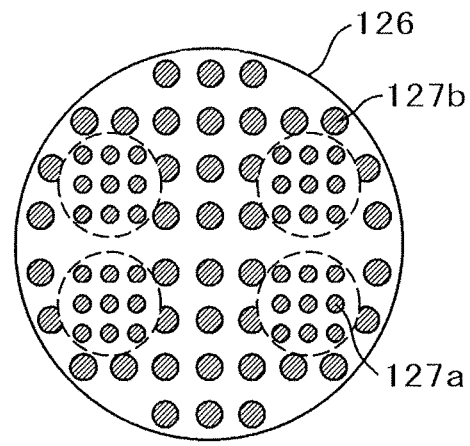
Figure 8D:
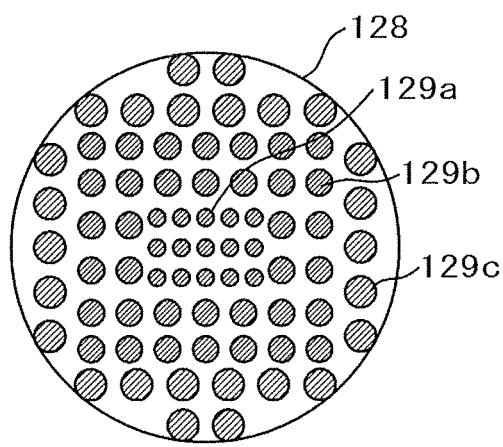

Also, by not limiting the first arranging pattern or the second arranging pattern to the central part in the hole 124, by placing like the culture sheet 126 in FIG. 8C, for example, by surrounding the first arranging pattern 127a in four parts with the second arranging pattern 127b, tissues with uniform size can be formed on the first arranging pattern 127a. In this way, combinations of the pillar diameter, the pillar pitch, and the arranging patterns make placing the most suitable arranging patterns depending on the objects, and culturing possible. In the same way, FIG. 8D indicates a culture sheet 128 with multi-step arranging patterns 129c, 129b, and 129a.

Next, by using FIG. 9, kinds of arranging pattern of protrusions (hereinafter, referred to as pillar pattern) in Examples described above are explained. As shown in FIG. 9, 11 kinds of arranging patterns are exemplified. As is obvious from FIG. 9, the pillar diameter and the pillar pitch are, 11 kinds, 0.18 to 20.0 µm, and 0.36 to 40.0 µm, of each, but are not limited to those. An example of liver cells cultured on these pillar patterns is shown in FIGS. 10A and 10B.

Furthermore, since, in culture on flat planes without pillar patterns, many cells are eliminated with media at the time of medium replacement during culturing, it is impossible to effectively obtain the desired culture cells. Therefore, the case is not depicted in FIG. 10A.

Figure 10A:
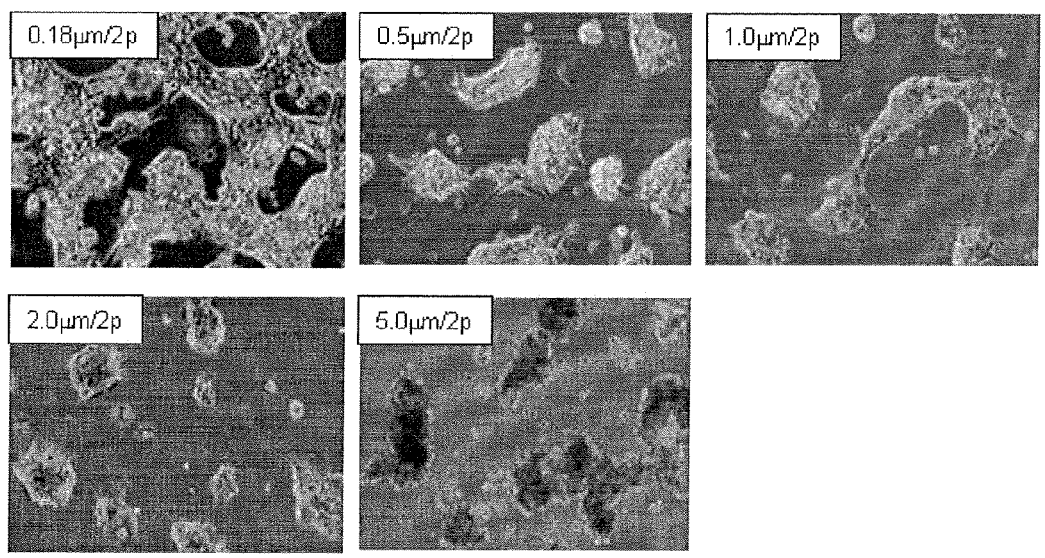
FIG. 10A shows views indicating cell culture results (cell appearances) when using culture sheets with different pillar diameters shown in FIG. 9.
Figure 10B:
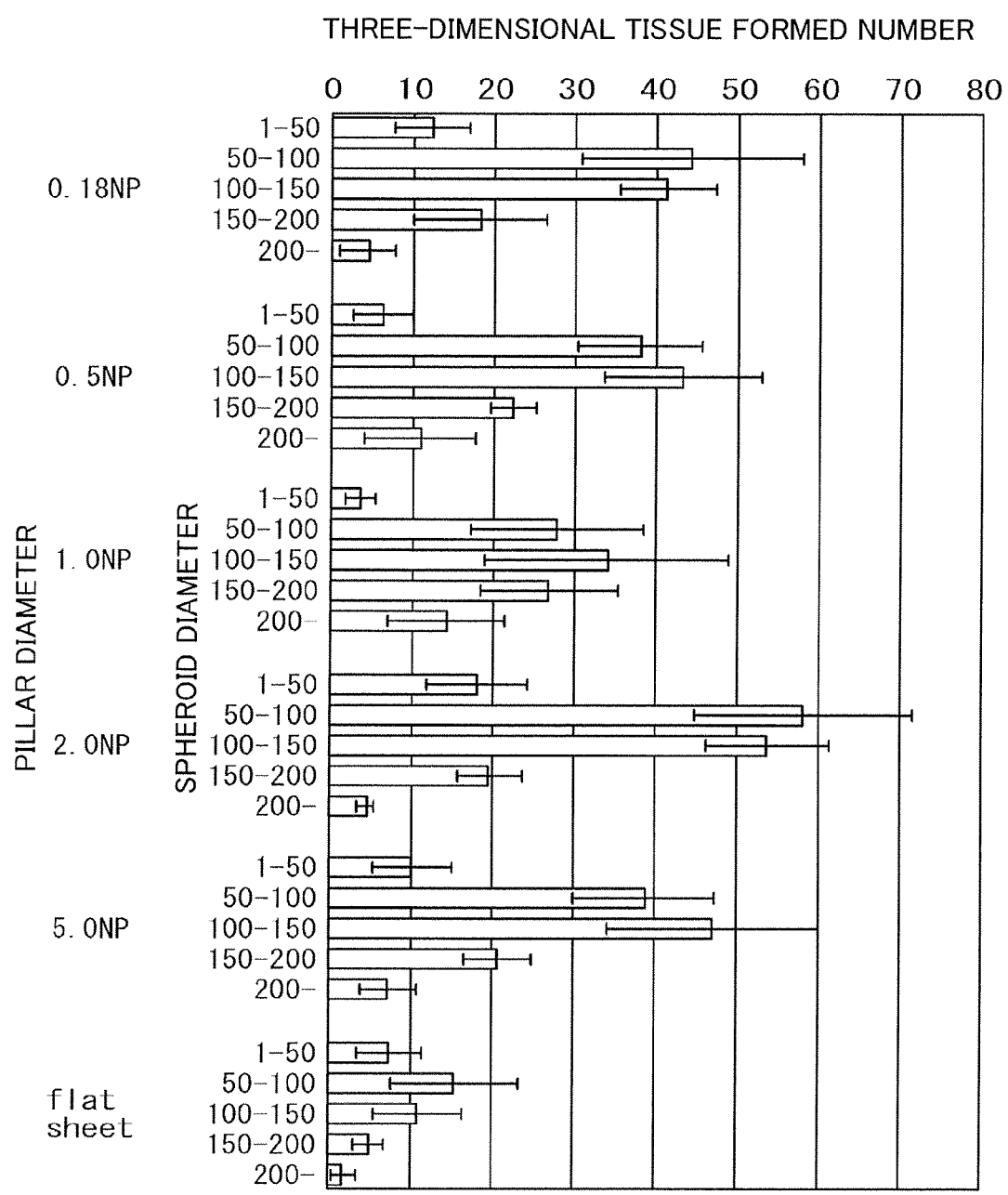
FIG. 10B shows views indicating cell culture results (formed cell numbers) when using culture sheets with different pillar diameters shown in FIG. 9.

FIG. 10A includes figures showing the appearances of cells cultured by using the culture sheet 100 with two times of pitches to the pillar diameters. As the results, when the pillar diameter is 0.18 µm, 0.5 µm, or 1.0 µm, not spherical but flat tissues were adhered to the substrate bottom planes. Meanwhile, when the pillar diameter is 2.0 µm or 5.0 µm, spherical three-dimensional tissues were formed in the substrates.

Furthermore, when spherical cells formed in substrates with the pillar diameter of 2.0 µm or 5.0 µm are compared, it was found that, in the substrate with the pillar diameter of 2.0 µm, cells were adhered to the substrate, and were in stable states. That is to say, as for cell adhesiveness, the larger pillar diameter shows smaller adhesiveness, and it is found that movement by cells is stimulated.

FIG. 10B is a view in which, as for numbers of three-dimensional tissues (spheroids) of liver cells formed in sheets with each pillar diameter, summed up results by formed diameters are shown. The sheet area is 4 square centimeters (2 cm×2 cm).

As for three-dimensional tissues of liver cells, in cell assays intended for drug screening, toxicity and metabolic testing instead of animal testing in the new drug developing field, cells with 50 to 100 µm diameter are preferable. Also in this example, in the substrate with pillar diameter of 2.0 µm, it is found that the formed number of cells with 50 to 100 µm diameter is the most, and the substrate is suitable.

However, under consideration described above, it was concluded that in order to form cells with 50 to 100 µm diameter, the pillar diameter of 2.0 µm is preferable, but the pillar diameter is not limited to the value. It was found that, at all pillar diameters used in the consideration, compared with the flat sheet case without any pillar, more cells with the stable shape were formed. Thus, by changing the pillar pattern, shapes of cells or tissues formed from cells, or adhesiveness to the substrate can be freely changed.

By applying the results described above, and as explained as for FIGS. 8A-8D of Example 4, by placing the first arranging pattern with smaller pillar diameter (pillar pitch) and the second arranging pattern with larger pillar diameter (pillar pitch) surrounding the first pattern in two stages, or by placing in multiple stages, it becomes possible to form a tissue with the intended shape at the intended position in the hole, by utilizing cell adhesiveness and motility of the cell itself.

Figure 11A:
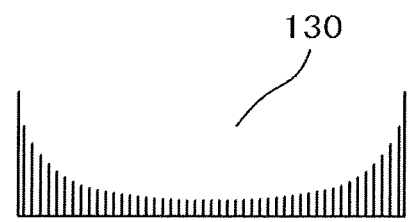
FIGS. 11A-11B show views of sloping nanopillar culture sheets being modifications of culture sheets used in the above Examples.

In addition, it is also possible that, by lowering the heights of the nanopillars with the same size of the pillar diameter from the peripheral zone to the central zone of the hole, and changing the heights gradually to make a gradient, and stimulating cells to assemble in the central part owing to gravity, a tissue is formed. In FIG. 11A, a culture sheet 30 being a modification in which the heights of nanopillars are gradually changed is shown. In this case, unlike the normal U-shaped culture substrates, since pillars exist, an effect that cells are held in the central part is obtained. Furthermore, it is also possible that, like the culture sheet 131 in FIG. 11B, by changing pillar diameters in the gradient, the effect is promoted.

Figure 11B:
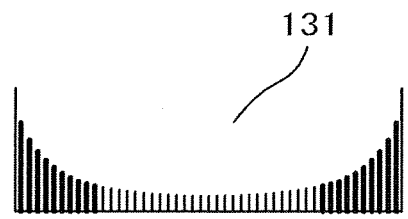

In the modification in FIGS. 11A-11B, the heights are gradually changed to make the gradient smooth, but the heights may also be changed in a step-by-step manner.

Figure 12A:
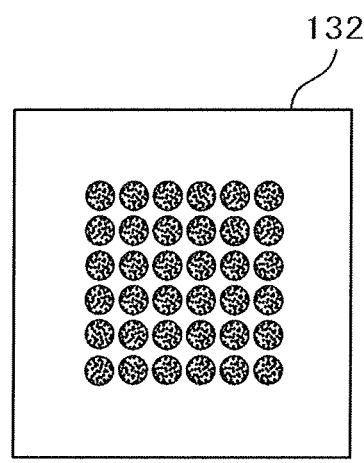
FIGS. 12A-12B show views indicating a well of surface tension-avoiding culture sheets being modifications of culture sheets used in the above Examples.
Figure 12B:
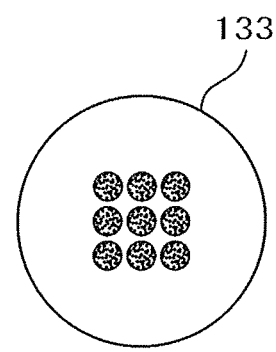

In addition, a plurality of holes assemble and constitute a culture plate (in case of a chamber slide, a square shaped plate, in case of a plate, a round shaped plate), but in culturing, due to the influence of surface tension, a difference in formation of the three-dimensional tissue is made between the central part and the peripheral part of the culture plate. That is, although a three-dimensional tissue is formed in the central part of the culture plate, in the peripheral part, a three-dimensional tissue may be formed for reasons that the medium amount in the part is increased due to surface tension, and oxygen feed amount is reduced and that higher water pressure is applied. To avoid this phenomenon, culture sheets 132 or 133 shown in FIGS. 12A and 12B, respectively, in which hole structures are held only in the central part of the culture plate, may be manufactured.

By forming such a culture sheet, a culture substrate with high culture efficiency and small manufacturing load can be obtained.

Example 5

Figure 15A:
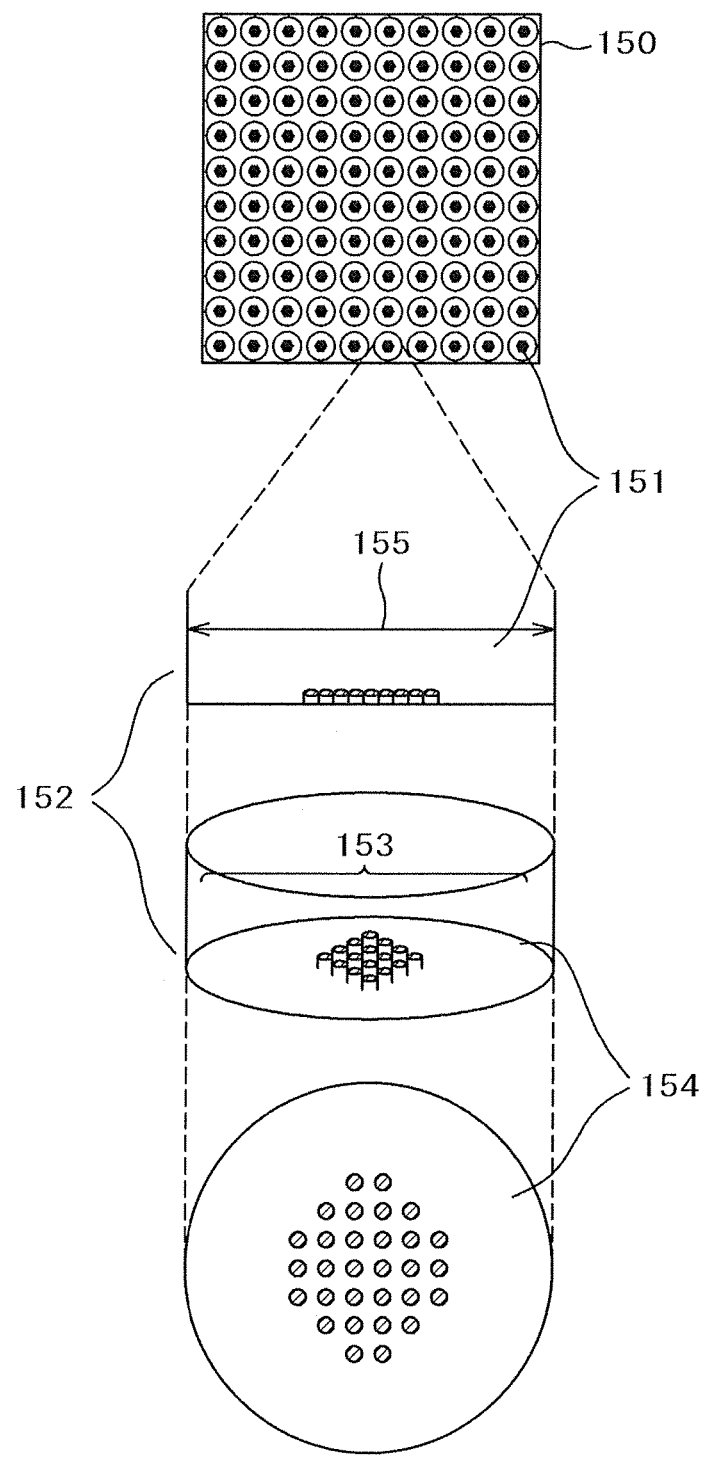
FIG. 15A is a view showing the culture sheet and the hole structure in the culture sheet in regard to Examples 5 and 6.
Figure 15B:
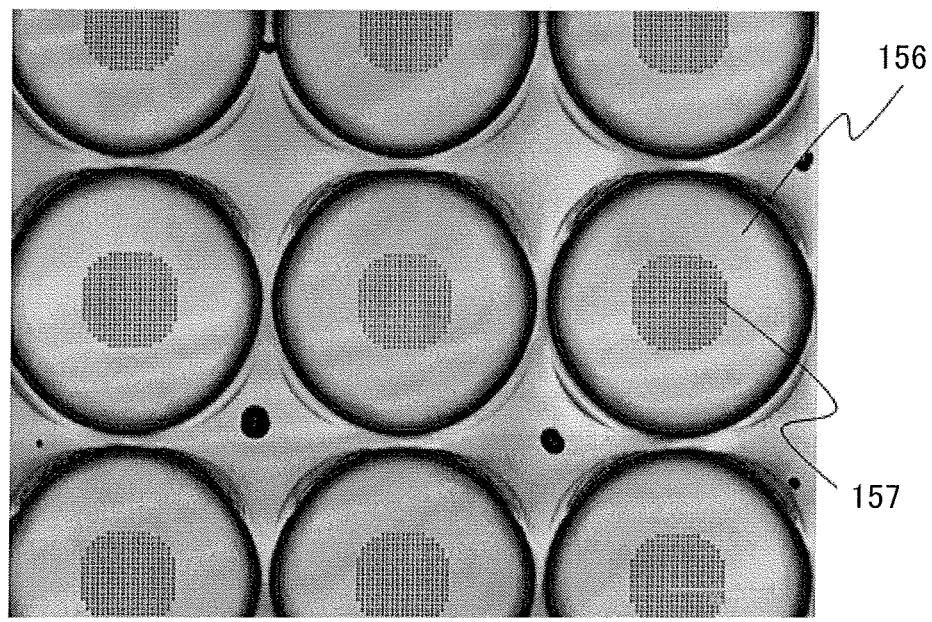
FIG. 15B is a view showing the culture sheet and the hole structure in the culture sheet in regard to Examples 5 and 6.
Figure 15C:
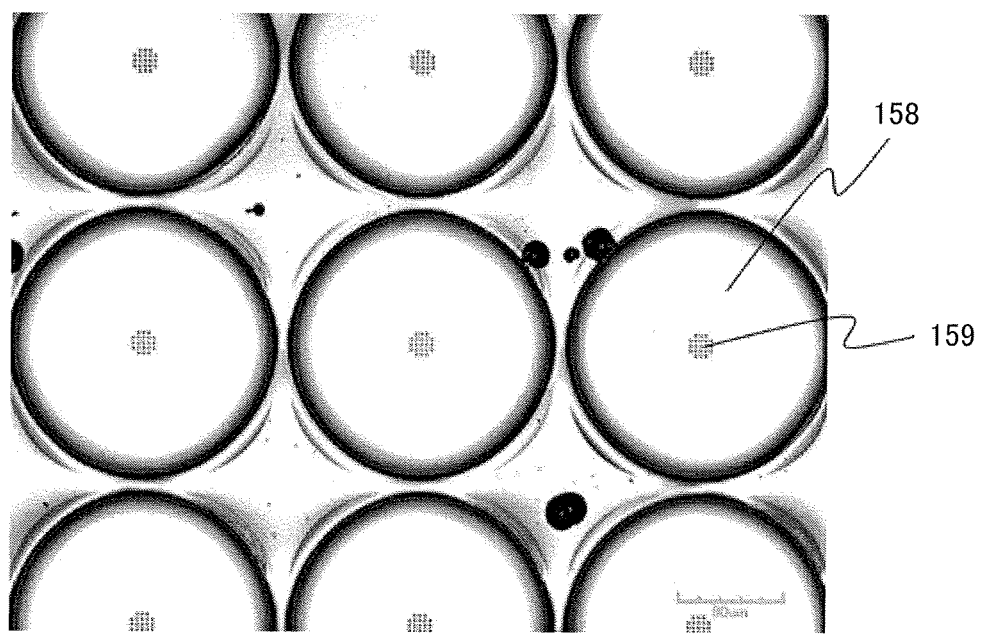
FIG. 15C is a view showing the culture sheet and the hole structure in the culture sheet in regard to Examples 5 and 6.

In FIG. 15A, FIG. 15B, and FIG. 15C, culture sheets of Example 5 are shown. Example 5 corresponds to, among various modifications shown in FIGS. 8A-8D of Example 4, a case of using a culture sheet in which the first arranging pattern 125a is flatly structured, and protrusions are placed only in the central parts of holes. That is, in the present example, since the culture sheet has a structure in which each culture region includes the first region and the second region surrounding the first region, only in the first regions, protrusions are arranged, and in the second regions, no protrusion is formed, spheroids being three-dimensional tissues with uniform diameters are held in the central part of the culture regions responding to the first regions, and three-dimensional tissues can be placed at the intended positions.

In the present example, a case in which protrusions are placed to the vicinity of the centers of the culture regions is shown. However, it is needless to say that the centers of the culture regions are not necessarily included by the protrusion parts, and protrusions may be arranged in desired regions in the culture regions. In addition, in the present example, the formed protrusion parts are nearly lozenge-shaped, but it is needless to say that they may be circularly, squarely, or polygonally shaped.

As shown in FIG. 15A, a culture sheet 150 is applied to a chamber slide being a culture sheet holding member. In the present example, culture sheets 150 were used in which the pillar height, the pillar diameter, and the pillar pitch, of the culture sheet were 1.0 µm, 2.0 µm, and 4.0 µm, respectively, in each hole 151 partitioned by partition walls 152 being the partition structures on the culture sheet, and the diameters of the protrusion assemblies were 80 µm and 20 µm.

FIG. 15A is a diagram of a scanning electro microscope photograph of the culture sheet 150 made in the present Example, and at the same time, shows a unit structure of holes 151 constituted by partition structures 152 existing a few sets per the culture sheet. In the same manner as in Examples described above, inside of the hole 101 constitutes a culture region with a cell tissue forming unit. A plurality of protrusions 153 held on bottom surfaces of holes 151 are comprised of a plurality of micro protrusions. In addition, the diameters of holes 151 are referred to as the hole diameters 155. In the culture sheet 150, the holes 151 furnished with the partition walls 152 described above, and a plurality of protrusions 153 formed in the holes 151 are integrally formed with the same material. Furthermore, in the same manner as in Examples described above, the holes 151 are not limited to be round-shaped, but may be square-shaped or others.

In each view in FIG. 15B and FIG. 15C, 156 and 158 indicate holes, and 157 and 159 indicate protrusion assemblies. Additionally, the culture sheet 150 is formed with materials having no bad influence on cells, and in the present example, polystyrene is used. However, it is needless to say that the materials are not limited to polystyrene.

As described above, since the holes 151 furnished with the partition walls 152 and a plurality of protrusions 153 formed in the holes 151 are integrally formed with a single material without bad influence on cells as the culture sheet 150, in the culture steps, cells can be grown without adhesions of foreign substances to cells. Additionally, since cells grow in each of the partition, forming cells with the uniform size becomes possible.

Also, since a plurality of protrusions are furnished in the surroundingly placed partition walls 152, cell motility originally held by cells is promoted, cells grow by the motility, and cell culture with keeping the activity and without influence of disturbance (stress) by such as rotational culture becomes possible.

If the culture regions are tried to be formed, with the holes 151 and the protrusion assemblies 153 as separate bodies, jointing of them by adhesion or deposition is required. For example, if they are jointed by adhesion, adhesive ingredients may be mixed into the culture regions, and have negative influences on produced cells. Also, in cases of deposition jointing, since inner diameters of holes 151 are diameters of extremely small regions at the cell forming level, it is considerably difficult to deposit with forming the object cell regions without damaging the partitions and protrusions. If the partitions and protrusions are damaged or deformed, needless stress may be added or cell motility itself may be disturbed in the cell forming steps.

Accordingly, also in the present example, it is desirable that the hole bottom surfaces 154, partition walls 152, and protrusions 153 to constitute holes 151 forming culture regions are integrally formed. Thus integral formation allows culture with elimination of unneeded ingredients other than needed ingredients for cell culture, and is suitable.

In addition, since the protrusions 153 in the present example have the similar structure as that of protrusions of Example 1 explained by using FIG. 2, explanation of enlarged views is omitted. In the present example, the height of the partition wall 152 being a partition structure is, for example, 70 µm, but, the height is not limited to the value, and may be suitably on the level that cells to be formed suitably cannot get over. Additionally, since the culture sheet 150 in the present example is manufactured in the similar manner as that in Example 1, detailed explanation of the manufacturing method is omitted.

Since it is needless to say that, also in the present example, as shown in FIG. 3, a chamber slide 109 applied by a culture sheet 150 can be manufactured, and chamber slides having a total configuration and sections of chief parts similar to that in FIG. 13A, FIG. 13B, and FIG. 13C can be obtained, explanation is omitted.

Example 6

Next, Example 6 is explained by using FIG. 4 and FIG. 5. Example 6 is an example in which the constitution and manufacturing example of a multi-well plate with the culture sheet 150 explained in Example 5 are shown. The constitution and manufacturing example of a multi-well plate were explained in detail by using FIG. 4 and FIG. 5. In the present example, the constitution and manufacturing method are fundamentally the same as that of Example 2, except that the culture sheet 150 instead of the culture sheet 100 used in Example 2 is used.

FIG. 4(a) is a bottom view of the frame 111 constituting the multi-well plate. In the frame 111 as the holding member of the culture sheet, in the surface space of about 125 mm wide and about 80 mm long and about 20 mm high, four holes in a vertical row and six holes in a horizontal row, totally 24 cylindrical holes 111a are molded. As the material, polystyrene is used.

The number of holes formed in the frame is normally from 6 to 1536. Since the number is changed depending on the application, also in the case of this frame, the number of holes is not limited to 24. In addition, the material of the frame is not limited to polystyrene.

In manufacturing of the culture substrate, the frame 111 and a culture sheet 150 in FIG. 15A are jointed with ultrasound deposition. The following processes and constitution or others are the same as that of Example 2.

In thus manufactured culture substrates, and in the culture sheet 150 described in FIG. 15A formed on the bottom surface of the frame 111 instead of the culture sheet 100, a plurality of holes 151 are formed, and a plurality of protrusions composed on the hole bottoms 154 are comprised of a plurality of micro protrusions 153. In addition, the diameters of the holes 151 are referred to as the hole diameters 155. In the culture sheet 150, the holes 151 furnished with partition walls 152 described above and a plurality of protrusions 153 formed in the holes 151 are integrally formed with the same material. Furthermore, the holes 151 are not limited to round shapes, and may be other shapes such as square shapes.

As described above, since the holes 151 furnished with the partition walls 152 and a plurality of protrusions 153 formed in the holes 151 are integrally formed with a single material without bad influence on cells as the culture sheet, in the culture steps, cells can be grown without adhesions of foreign substances to cells. Additionally, since cells grow in each of the partition, forming cells in uniform size becomes possible. Also, since a plurality of protrusions are furnished in the surroundingly placed partition, cell motility originally held by cells is promoted, cells grow by the motility, and cell culture with keeping the activity and without influence of disturbance (stress) by such as rotational culture becomes possible.

As described above, it is desirable, also in the present example, that holes 151 and a plurality of protrusions 153 to constitute culture regions are integrally formed. Thus integral formation makes carrying out of culture with elimination of influences of unneeded ingredients other than needed ingredients for cell culture possible, and is suitable.

Since also a total configuration view and sectional views of chief parts of the multi-well plate with the culture sheet in the present example, in the same way as in Example 2, become as shown in FIG. 14A, FIG. 14B, FIG. 14C, and FIG. 14D, explanation is omitted.

Example 7

Next, as Example 7, application cases of culture substrates manufactured in Example 5 and Example 6 to cell tissue culture is explained. Previously, as Example 3, application cases of culture substrates manufactured in Example 1 and Example 2 to cell tissue culture were shown. The difference between the present example and Example 3 is that, in the present example, culture substrates with the culture sheets 150 instead of the culture sheets 100 are used. Since other points share explanation in common, the explanation is omitted.

Furthermore, it is needless to say that the culture flow chart using the culture substrates thus obtained, except that the culture sheet 150 is used, is the same as that shown in FIGS. 6A-6E.

Figure 16:
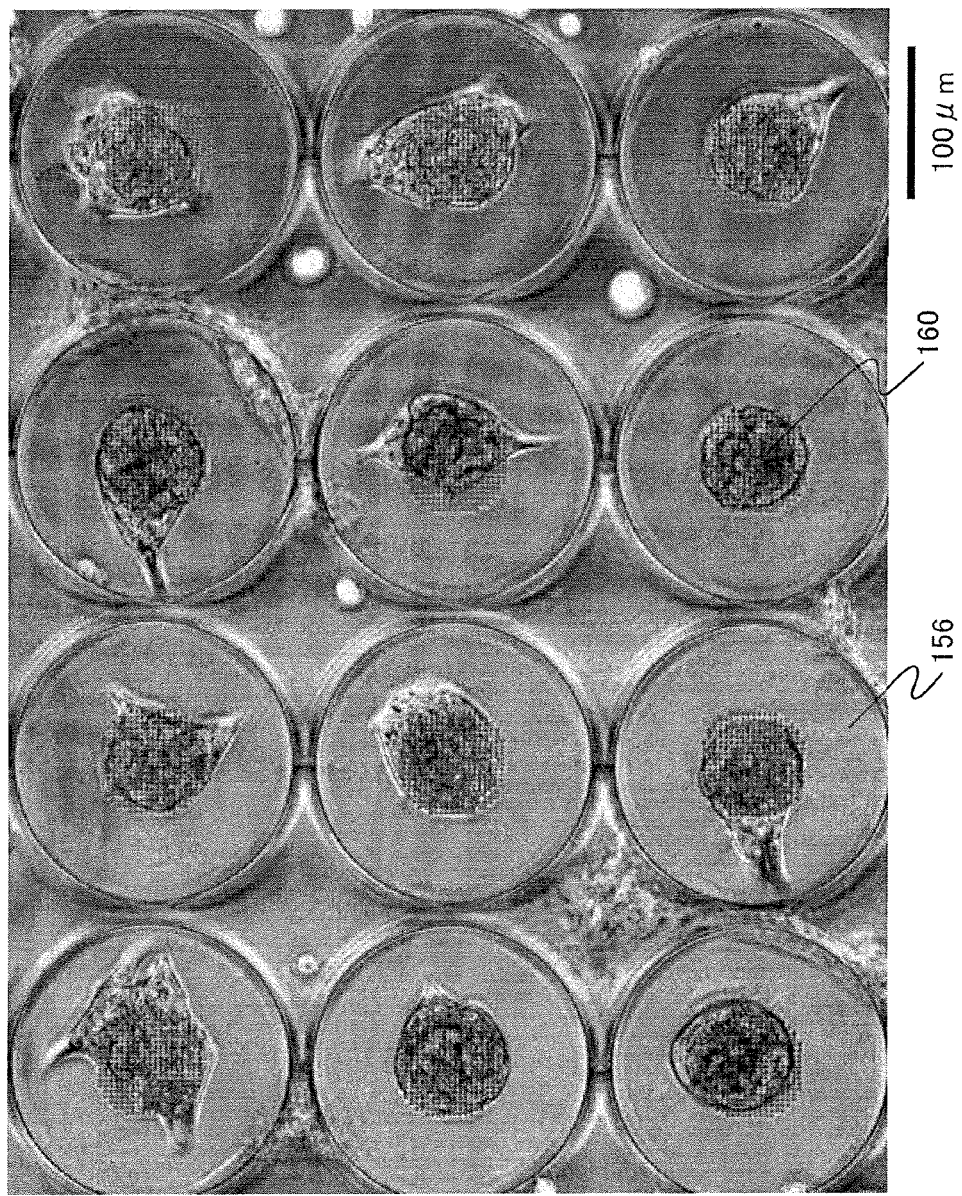
FIG. 16 is a view showing the photogram of the liver cell three-dimensional tissues according to the liver cell culturing flow with the culture sheet in regard to Example 7.
Figure 17:
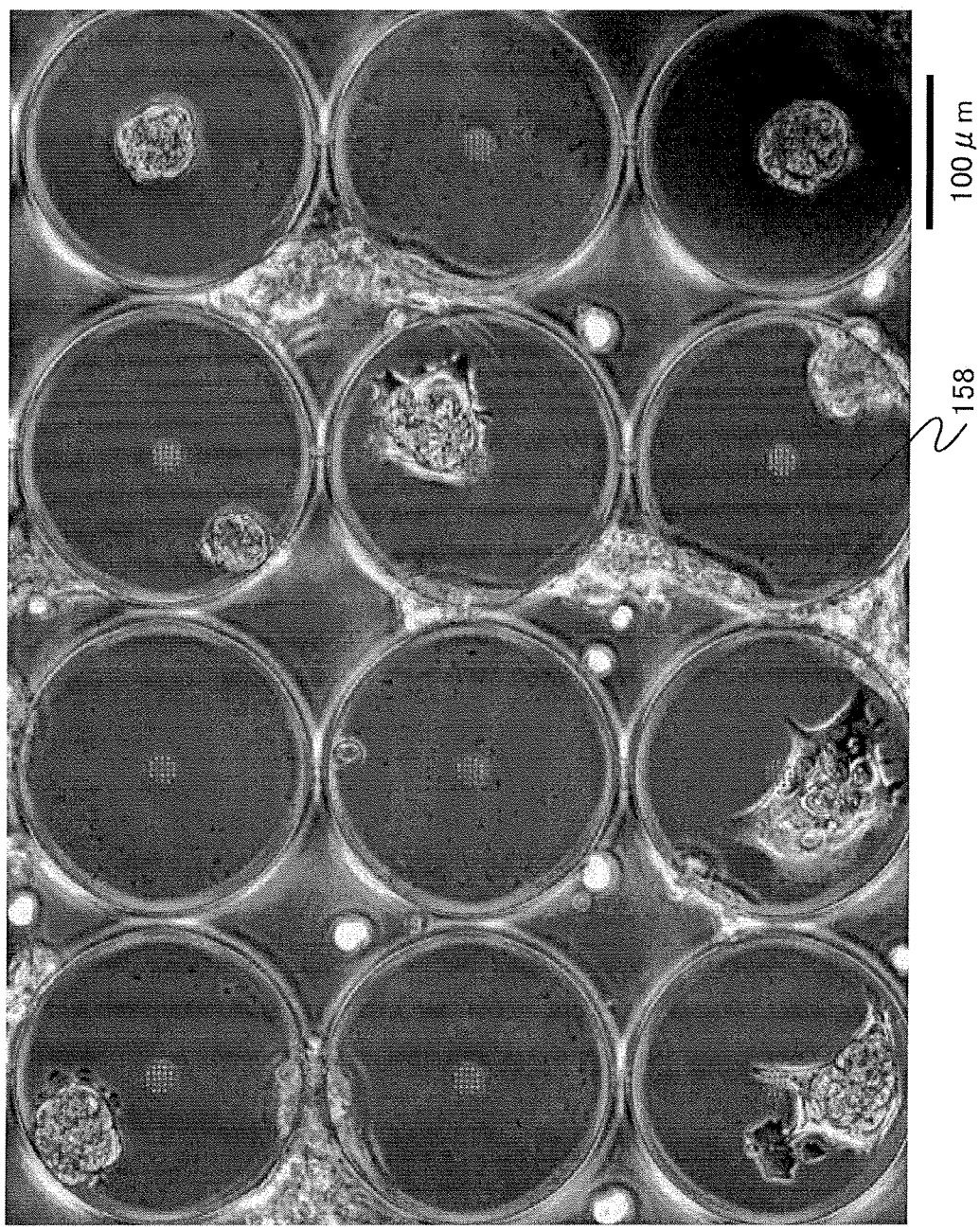
FIG. 17 is a view showing the photogram of the liver cell three-dimensional tissues according to the liver cell culturing flow with the culture sheet in regard to Example 7.
Figure 18:
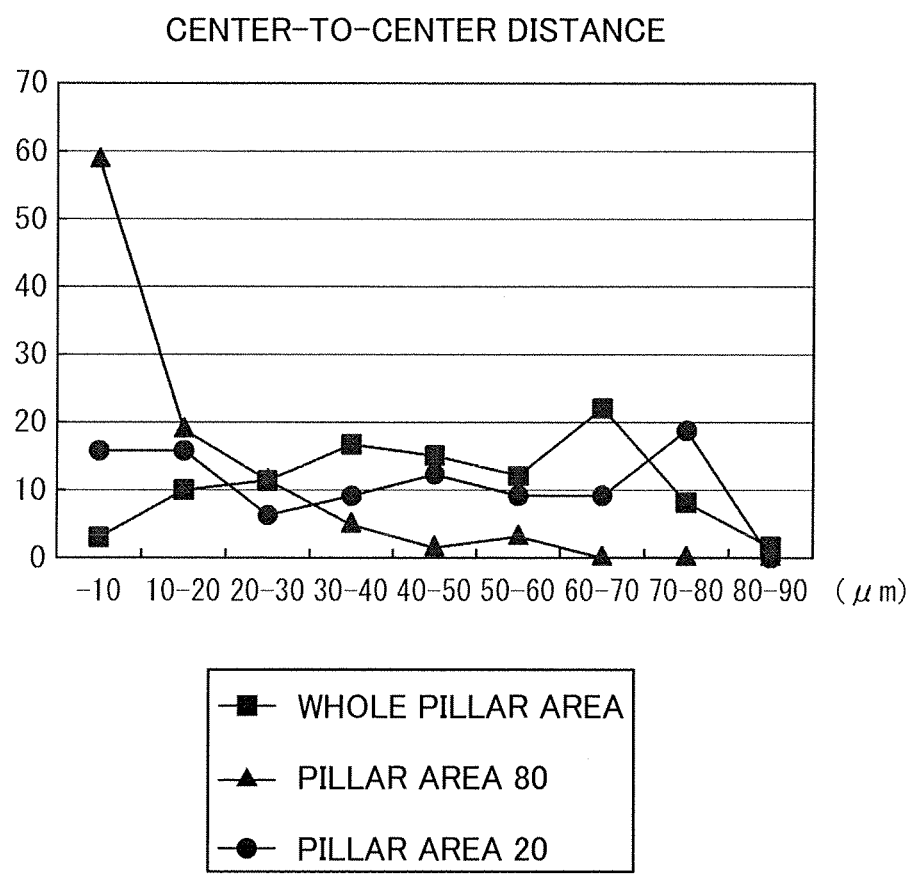
FIG. 18 is a view showing the distances between the centers of the liver cell three-dimensional tissues according to the liver cell culturing flow with the culture sheet and the centers of the hole structures in regard to Example 7.

By using FIG. 16, FIG. 17, and FIG. 18, results of culturing in which culture substrates of the present example are used, are explained. In the present example, in the culture sheet 150 in which nanopillars with the pillar width of 2.0 μm are circularly arranged with the diameter of 80 μm in the central parts of the holes 151, as shown in FIG. 16, spheroids with uniform diameters 160 are held in the central parts of the holes 156. In addition, as shown in FIG. 17, in the culture sheet 150 in which nanopillars of the same size are circularly arranged with the diameter of 20 μm in the central parts of the holes 158, spheroids were not held in the central parts.

As obvious from the above result, without application of special chemical substances to the surface of the culture sheet, and by static culturing with less stress for cells, spherical three-dimensional tissues of such a uniform size were formed. Since this method is considered not to eliminate the cellular activity originally held, it is an effective culturing method for such as cell assay.

In FIG. 18, results of measurement of the center-to-center distances between holes 151 and spheroids by using three kinds of sheets with whole area nanopillar, pillar area diameter of 80 μm, and pillar area diameter of 20 μm, are shown. In FIG. 18, the horizontal axis shows the width (μm) of spheroids, and the vertical axis shows the center-to-center distances between holes 151 and spheroids (μm). As FIG. 18 shows, it is found that, compared to other two kinds of culture sheets, in the culture sheet with pillar area diameter of 80 μm, spheroids are obviously placed in the central parts of the holes. It became obvious that when the hole diameter and the central nanopillar areas are suitably determined, spheroids of uniform size are held in the central parts of holes.

INDUSTRIAL APPLICABILITY

The present invention is extremely useful as a technique to culture animal cells and plant cells by using the culture substrate, and to form globular tissues (three-dimensional tissues) and monolayer tissues (two-dimensional plain tissues) of cells.

REFERENCE SIGNS LIST 100, 123, 126, 128, 130, 131, 132, 133, 150: Culture Sheet
101, 124, 151, 156, 156: Hole
102, 152: Partition Wall
103, 153, 157, 159: Protrusion/Protrusion assembly
104, 154: Bottom Surface
105, 155: Hole Diameter
106: Pillar Diameter
107: Pillar Pitch
108: Pillar Height
109: Chamber Slide
110: Surgical Adhesive
111: Frame
111a: Hole part formed in the Frame
112: Protrusion for Film Fixation
113: Rib Structure
114: Holes in the Culture Sheet
115: Cell Culture Plate
116: Type I Collagen Solution
117: Pressure Reduction Vessel
118: Pump for Pressure Reduction
119: Flushing Saline (PBS (−))
120: Medium
121: Liver Cell
122: Liver Cell Spheroid
125a, 125b, 127a, 129b, 129b, 129c: Protrusion Arranging Pattern
1111: Anti-slip Part
1112: Jointing Part
1113: Cut Part

The invention claimed is:
1. A culture substrate for culturing cells, comprising:
a culture sheet; and
a culture sheet holding section that is jointed to the culture sheet, and holds the culture sheet;
wherein the culture sheet has a plurality of culture regions, and in the culture regions, a plurality of protrusions are formed,
wherein a plurality of hole structures are formed by a plurality of partitions that are higher than the protrusions, and lower than a sidewall formed by the culture sheet holding section, and
wherein a plurality of first regions and second regions are disposed in one or more of the culture regions, and width/diameter ratios of the protrusions in the first regions are different from those in the second regions in each of the one or more of the culture regions.

2. The culture substrate according to claim 1 wherein a frame that surrounds the culture sheet is formed by the sidewall.

3. The culture substrate according to claim 2, wherein the frame is formed in the culture sheet holding section.

4. The culture substrate according to claim 2, wherein the frame is square-shaped or circular-shaped.

5. The culture substrate according to claim 1, wherein the culture sheet holding section and the culture sheet are jointed with ultrasound deposition.

6. The culture substrate according to claim 1, wherein the partitions surround the culture regions.

7. The culture substrate according to claim 1, wherein the width/diameter ratios of the protrusions change gradually in each of the one or more of the culture regions.

8. The culture substrate according to claim 1, wherein pitches of the protrusions are different in each of one or more of the culture regions.

9. The culture substrate according to claim 1, wherein pitches of the protrusions change gradually in each of one or more of the culture regions.

10. The culture substrate according to claim 1, wherein heights of the protrusions are different in each of one or more of the culture regions.

11. The culture sheet according to claim 1, wherein heights of the protrusions are configured to make a gradient in each of the one or more of the culture regions.

12. The culture substrate according to claim 1, wherein the partitions and the protrusions in the culture sheet are integrally formed with the same material.

13. A culture substrate for culturing cells, comprising:
a culture sheet; and
a culture sheet holding section that is jointed to the culture sheet, and holds the culture sheet,
wherein the culture sheet has a plurality of culture regions, and in the culture regions, a plurality of protrusions are formed,
wherein a frame surrounding the culture regions is formed in the culture sheet holding section, and a plurality of hole structures are formed by a plurality of partitions that are higher than the protrusions, and lower than the frame, and
wherein a plurality of first regions and second regions are disposed in one or more of the culture regions, and pitches of the protrusions in the first regions are different from those in the second regions in each of the one or more culture regions.

14. The culture substrate according to claim 13, wherein the culture sheet holding section and the culture sheet are jointed with ultrasound deposition.

15. The culture substrate according to claim 13, wherein the partitions and the protrusions in the culture sheet are integrally formed with the same material.

16. A cell culturing method, the method comprising:
furnishing a culture substrate with a culture sheet, and a culture sheet holding section that is jointed to the culture sheet and holds the culture sheet,
where the culture sheet has a plurality of culture regions, and a plurality of protrusions are formed in the culture regions,
where a plurality of hole structures are formed by a plurality of partitions that are higher than the protrusions, and lower than a sidewall formed by the culture sheet holding section, and
where a plurality of first regions and second regions are disposed in one or more of the culture regions, and width/diameter ratios of the protrusions in the first regions are different from those in the second regions in each of the one or more of the culture regions;
disseminating cells into each of the plurality of culture regions; and
forming three-dimensional tissues of the cells in each of the plurality of culture regions by.

17. The cell culturing method according to claim 16, wherein the cells include embryonic stem cells, induced Pluripotent Stem cells (iPS cells), or liver cells.

18. A cell culturing method according to claim 16, wherein the culture substrate has a frame surrounding the culture sheet, which is formed by the sidewall.

19. The cell culturing method according to claim 16, wherein the partition and the plurality of protrusions in the culture sheet are integrally formed with the same material.

* * * * *